(12) United States Patent
Gharbaoui et al.

(10) Patent No.: US 7,425,630 B2
(45) Date of Patent: Sep. 16, 2008

(54) PROCESSES FOR PREPARING PYRAZOLO[3,4-D]PYRIMIDINE ETHERS

(75) Inventors: Tawfik Gharbaoui, Escondido, CA (US); Dipanjan Sengupta, San Diego, CA (US); Edward A. Lally, San Diego, CA (US); Naomi S. Kato, San Diego, CA (US); Marlon Carlos, Santee, CA (US); Natalie Rodriguez, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 179 days.

(21) Appl. No.: 11/331,372

(22) Filed: Jan. 12, 2006

(65) Prior Publication Data

US 2006/0154940 A1 Jul. 13, 2006

Related U.S. Application Data

(60) Provisional application No. 60/643,712, filed on Jan. 13, 2005.

(51) Int. Cl.
*C07D 401/12* (2006.01)
*C07D 231/38* (2006.01)

(52) U.S. Cl. .................................. 544/262; 548/371.7
(58) Field of Classification Search ................. 544/262; 548/371.7
See application file for complete search history.

(56) References Cited

U.S. PATENT DOCUMENTS

| 6,660,744 B1 | 12/2003 | Hirst et al. |
| 7,132,426 B2 * | 11/2006 | Jones et al. ............... 514/262.1 |
| 2002/0156081 A1 | 10/2002 | Hirst et al. |
| 2005/0209251 A1 | 9/2005 | Linker et al. |

FOREIGN PATENT DOCUMENTS

| EP | 0053678 A1 | 10/1981 |
| EP | 0 050 671 | 5/1982 |
| EP | 0 123 402 | 10/1984 |
| EP | 0 526 004 | 2/1993 |
| EP | 0772087 A1 | 7/1997 |
| WO | WO 81/03174 | 11/1981 |
| WO | WO03093269 | 11/2003 |
| WO | WO2004009602 A1 | 1/2004 |
| WO | WO2005007658 | 7/2004 |
| WO | WO2006050946 A1 | 5/2006 |

OTHER PUBLICATIONS

Cheng et al., "Potential purine antagonists. VI. Synthesis of 1-alkyans 1-ary-4substituted pyrazolo[3,4-d]pyrimidines", Journal of Organic Chemistry, vol. 21:1240-56 (1956).
Cheng et al., "Potential purine antagonists. XII. Synthesis of 1-alkyl(aryl)-4,6-disubstituted pyrazolo[3,4-d]pyrimidines", Journal of Organic Chemistry, vol. 23:852-61 (1957).
Markwalder et al., "Synthesis and biological evaluation of 1-aryl-4,5-dihydro-1H-pyrazolo[3,4-d]pyrimidin-4-one inhibitors of cyclin-dependent kinases", J. Med. Chem., vol. 47:5894-911 (2004).
Mitsunobu, Oyo, "The Use of diethyl azodicarboxylate and triphenylphosphine in synthesis and transformation of natural products", Synthesis, Jan. 1981 pp. 1-28.
Peat et al., "Novel pyrazolopyrimidine derivatives as GSK-3 inhibitors", Bioorganic & Medicinal Chemistry Letters 14:2121-5 (2004).
International Search Report for PCT/US2006/001020 (2006).
Bol'v, et al., "A new synthetic approach to fused pyrimidin-4-ones", Institute of Organic Chemistry, National Academy of Sciences of Ukraine, Murmanskaya str. 5, Kiev, 02094, Ukrain; Abstract only http://conf.iflab.kiev.ua/eng/reports/show/?id=348.
Kolosov et al., "the interaction between 4-phenyl-5-acetyl-6-methyl-3,4-dihydroprimidine-2-one and 4-brombenzaldehyde", Institute of Organic Chemistry, Kharkiv, National V.N.Karazin University, Ukraine, 61077, Kharkiv-007, Svobody sq., 4; Abstract only at http://conf.iflab.kiev.ua/eng.reports/show/?id=926.
Niementowski, *J. Prakitka Chem.*, [2] "Synthesen von Chinazolinverbindugen" (1895), 51, 564-572.
3rd Party Opposition Filed by the Asociacion de Laboratorios Famaceuticos (ALAFAR) in Corresponding Ecuadorian Patent Appln. No. 07-7589, 5 pgs.

* cited by examiner

*Primary Examiner*—Bruck Kifle
(74) *Attorney, Agent, or Firm*—Fish & Richardson P.C.; Lyle Spruce; Christine A. Goddard

(57) ABSTRACT

The present invention relates to processes for preparing pyrazolo[3,4-d]pyrimidine ether compounds that are modulators of glucose metabolism and therefore useful in the treatment of metabolic disorders such as diabetes and obesity.

74 Claims, No Drawings

PROCESSES FOR PREPARING PYRAZOLO[3,4-D]PYRIMIDINE ETHERS

CROSS REFERENCE TO RELATED APPLICATIONS

This application claims the benefit of U.S. Ser. No. 60/643,712, filed Jan. 13, 2005, the disclosure of which is incorporated herein by reference in its entirety.

FIELD OF THE INVENTION

The present invention relates to processes for preparing pyrazolo[3,4-d]pyrimidine ether compounds that are modulators of glucose metabolism and therefore useful in the treatment of metabolic disorders such as diabetes and obesity.

BACKGROUND OF THE INVENTION

Modulation of G-protein coupled receptors has been well-studied for controlling various metabolic disorders. Small molecule modulators of the receptor RUP3, a G-protein coupled-receptor described in, for example, GenBank (see, e.g., accession numbers XM_066873 and AY288416), have been shown to be useful for treating or preventing certain metabolic disorders. In particular, pyrazolo[3,4-d]pyrimidine ethers and similar compounds, which are described in U.S. Ser. No. 10/890,549 are shown to be effective modulators of the RUP3 receptor and are useful in the treatment of various metabolic-related disorders such as type I diabetes, type II diabetes, inadequate glucose tolerance, insulin resistance, hyperglycemia, hyperlipidemia, hypertriglyceridemia, hypercholesterolemia, dyslipidemia or syndrome X. The aromatic ethers are also useful in controlling weight gain, controlling food intake, and inducing satiety in mammals. The promising nature of these RUP3 modulators in treating or preventing a number of common diseases evidences a need for more efficient processes of making these compounds. The processes described herein are directed toward this and other current needs.

SUMMARY OF THE INVENTION

The present invention provides, inter alia, processes for preparing compounds of Formula I:

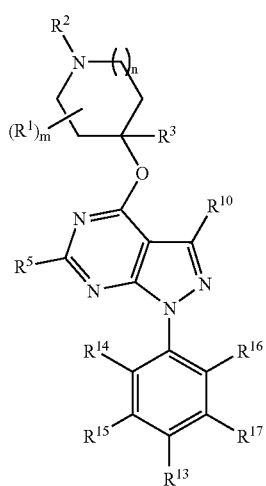

wherein constituent variables are provided herein; comprising reacting a compound of Formula II:

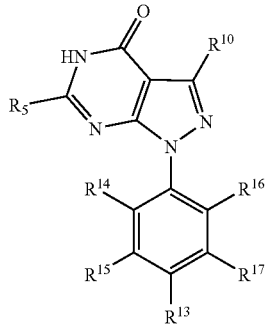

with a compound of Formula III:

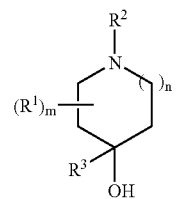

in the presence of a trisubstituted phosphine and a compound having the Formula A':

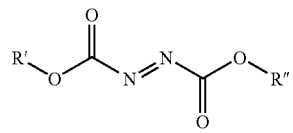

wherein R' and R" are each, independently, $C_{1-10}$ alkyl or $C_{3-7}$ cycloalkyl; to form the compound of Formula I.

The present invention further provides processes for preparing compounds of Formula II; by reacting a compound of Formula IV:

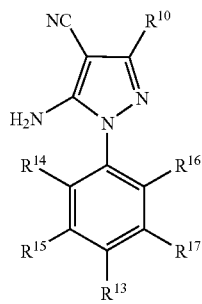

with $R^5CO_2H$ to form the compound of Formula II.

The present invention further provides a process for preparing a compound of Formula IV by reacting a compound of Formula V:

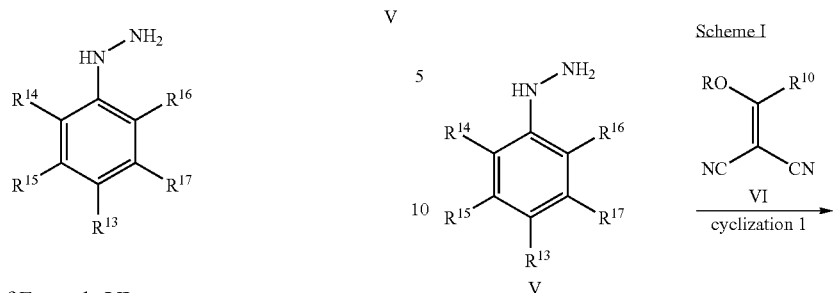

with a compound of Formula VI:

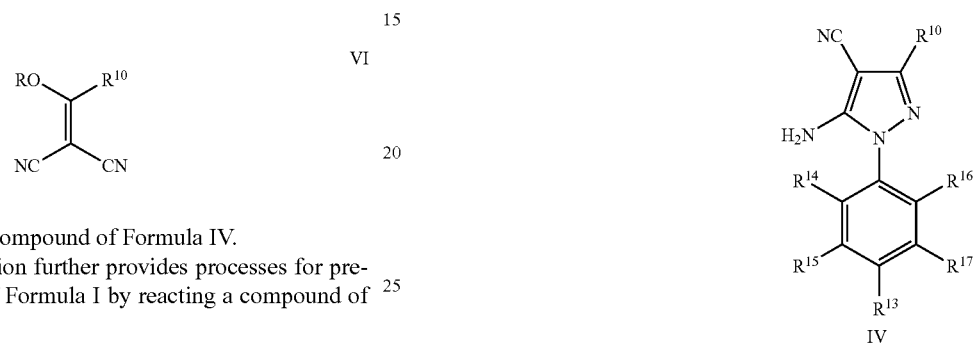

thereby forming the compound of Formula IV.

The present invention further provides processes for preparing compounds of Formula I by reacting a compound of Formula IIa:

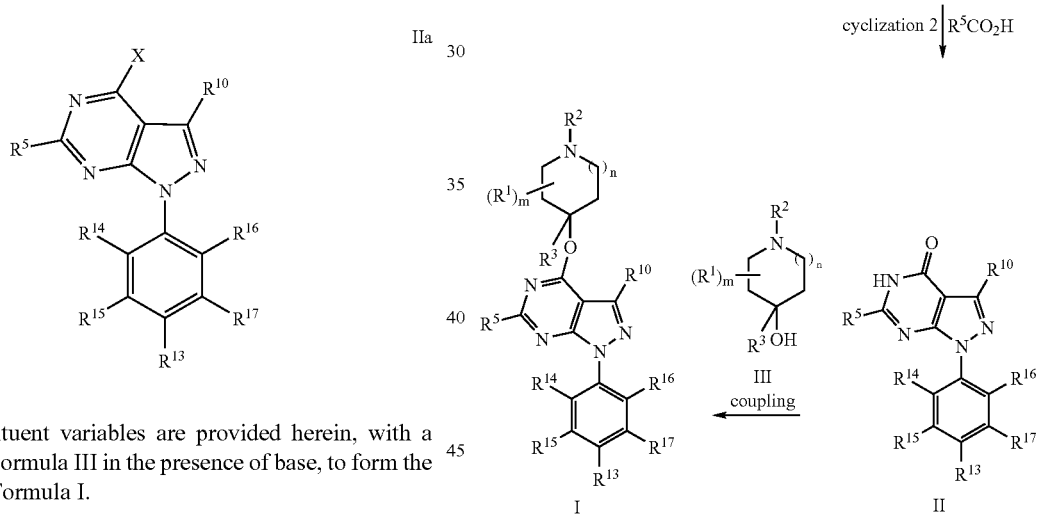

wherein constituent variables are provided herein, with a compound of Formula III in the presence of base, to form the compound of Formula I.

The present invention further provides processes for preparing compounds of Formula IIa by reacting a compound of Formula II with a halogenating reagent to form the compound of Formula IIa.

The present invention further provides bulk samples of compounds prepared by the processes described herein

DETAILED DESCRIPTION

The present invention is directed to processes and intermediates for the preparation of aromatic ethers that are useful as RUP3 modulators for the treatment of metabolic disorders such as diabetes and obesity.

Example processes and intermediates of the present invention are provided below in Schemes I and II, wherein constituent members of the formulae depicted therein are defined below.

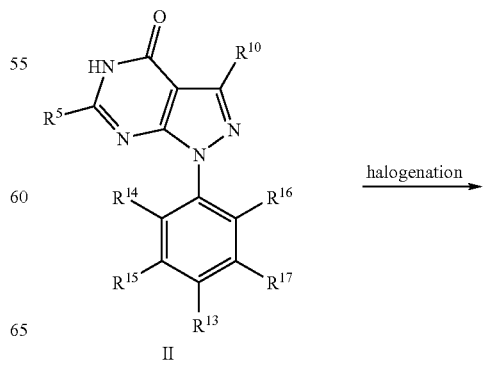

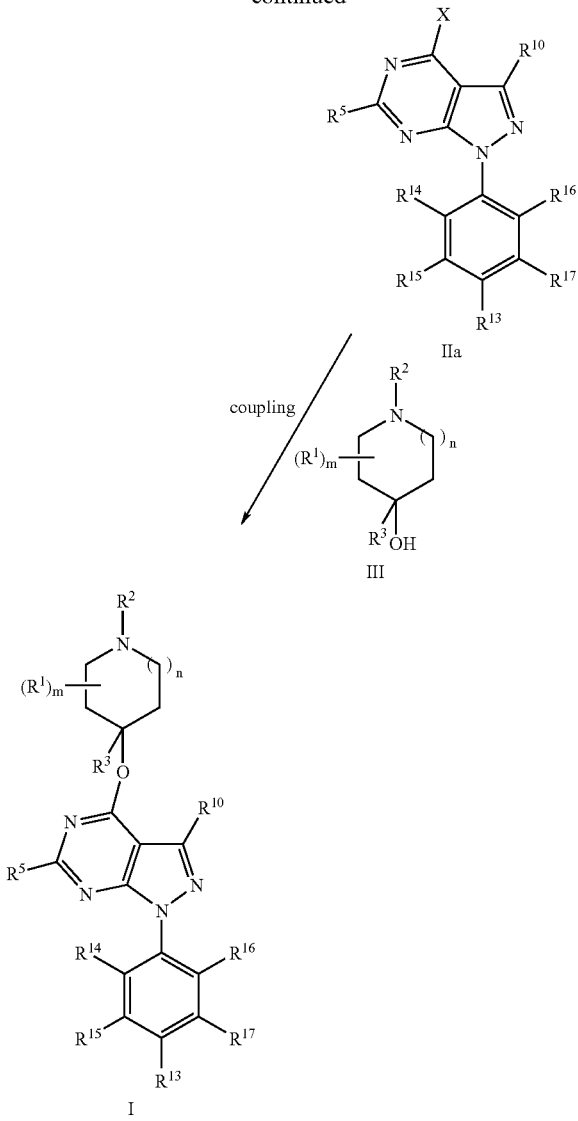

The present invention provides processes, such as exemplified in Schemes I and II, involving compounds of Formulas I, II, IIa, III, IV, V, and VI or salt forms thereof, wherein:

X is halo;

R is $C_{1-4}$ alkyl;

$R^1$ is $C_{1-3}$ alkyl, $C_{1-4}$ alkoxy, carboxy, cyano, $C_{1-3}$ haloalkyl, or halogen;

$R^2$ is $-R^{24}$, $-CR^{25}R^{26}C(O)-R^{24}$, $-C(O)CR^{25}R^{26}-R^{24}$, $-C(O)-R^{24}$, $-CR^{25}R^{26}C(O)NR^{27}-R^{24}$, $-NR^{27}C(O)CR^{25}R^{26}-R^{24}$, $-C(O)NR^{25}-R^{24}$, $-NR^{25}C(O)-R^{24}$, $-C(O)O-R^{24}$, $-OC(O)-R^{24}$, $-C(S)-R^{24}$, $-C(S)NR^{25}-R^{24}$, $-NR^{25}C(S)-R^{24}$, $-C(S)O-R^{24}$, $-OC(S)-R^{24}$, $-CR^{25}R^{26}-R^{24}$, or $-S(O)_2-R^{24}$;

$R^3$ is H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl;

$R^5$ and $R^{10}$ are each, independently, H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino or nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclic-sulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy; and wherein said $C_{1-7}$ alkyl and $C_{1-4}$ alkylcarboxamide are each optionally substituted with 1 to 5 substituents selected from $C_{1-4}$ alkoxy and hydroxy; or $R^{13}$ is a group of Formula (A):

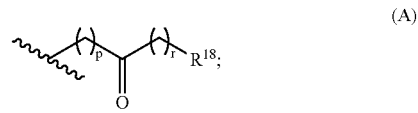

$R^{14}$, $R^{15}$, $R^{16}$, and $R^{17}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl or nitro; or two adjacent $R^{14}$, $R^{15}$, $R^{16}$ and $R^{17}$ together with the atoms to which they are attached form a 5-, 6- or 7-membered fused cycloalkyl, cycloalkenyl or heterocyclic group, wherein said 5-, 6- or 7-membered fused group is optionally substituted with halogen;

$R^{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl is optionally substituted with 1 to 5 substituents selected independently from $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;

$R^{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-4}$ alkoxy, $C_{1-7}$ alkyl, $C_{1-4}$ alkylamino, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, nitro, and phenyl;

$R^{25}$, $R^{26}$ and $R^{27}$ are each, independently, H or $C_{1-8}$ alkyl;

m is 0, 1, 2, 3, or 4;

n is 0 or 1; and p and r are each, independently, 0, 1, 2 or 3.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., n, m, $R_1$, $R_2$, $R_3$, $R_5$, $R_{10}$, $R_{13}$, $R_{14}$, $R_{15}$, $R_{16}$, $R_{17}$, etc.) contained within the generic chemical formulae described herein [e.g. I, (A), A', II, III, IV, V, etc.] and process steps disclosed herein are specifically embraced by the present invention just as if they were explicitly disclosed, to the extent that such combinations embrace compounds that result in stable compounds (ie., compounds that can be isolated, characterized and tested for biological activity). In addition, all subcombinations of the chemical groups listed in the embodiments describing such variables, as well as all subcombinations of process steps, are also specifically embraced by the present invention just as if each of such subcombination of chemical groups and process steps were explicitly disclosed herein.

In some embodiments, n is 1.

In some embodiments, m is 0.

In some embodiments, $R^2$ is —C(O)O—$R^{24}$.

In some embodiments, $R^2$ is —C(O)O—$R^{24}$ and $R^{24}$ is $C_{1-8}$ alkyl or $C_{3-7}$ cycloalkyl.

In some embodiments, $R^2$ is —C(O)O—$R^{24}$ and $R^{24}$ is $C_{1-4}$ alkyl.

In some embodiments, $R^2$ is —C(O)O—$R^{24}$ and $R^{24}$ is methyl, ethyl, or prop-1-yl, prop-2-yl.

In some embodiments, $R^2$ is —C(O)O—$R^{24}$ and $R^{24}$ is prop-2-yl.

In some embodiments, $R^3$ is H.

In some embodiments, $R^5$ is H.

In some embodiments, $R^{10}$ is H.

In some embodiments, $R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol.

In some embodiments, $R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, or $C_{1-4}$ alkylsulfonyl.

In some embodiments, $R^{13}$ is $C_{1-4}$ alkylsulfinyl or $C_{1-4}$ alkylsulfonyl.

In some embodiments, $R^{13}$ is $C_{1-4}$ alkylsulfonyl.

In some embodiments, $R^{13}$ is methylsulfonyl or ethylsulfonyl.

In some embodiments, $R^{13}$ is methylsulfonyl.

In some embodiments, $R^{14}$, $R^{15}$, $R^{16}$, and $R^{17}$ are each, independently, H, $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro.

In some embodiments, $R^{14}$, $R^{15}$, $R^{16}$, and $R^{17}$ are each, independently, H, $C_{1-4}$ alkoxy, $C_{1-8}$ alkyl, cyano, halogen, hydroxyl, or nitro.

In some embodiments, $R^{14}$, $R^{15}$, $R^{16}$, and $R^{17}$ are each, independently, H or halogen.

In some embodiments, $R^{14}$ is other than H.

In some embodiments, $R^{14}$ is halogen.

In some embodiments, $R^{14}$ is F.

In some embodiments, $R^{15}$, $R^{16}$, and $R^{17}$ are each H and $R^{14}$ is other than H.

In some embodiments, $R^{13}$ is $C_{1-4}$ alkylsulfonyl; $R^{15}$, $R^{16}$, and $R^{17}$ are each H; and $R^{14}$ is halogen.

In some embodiments, R is methyl or ethyl;

In some embodiments, R is ethyl;

In some embodiments, X is Cl;

In some embodiments:

$R^2$ is —C(O)O—$R^{24}$;

$R^3$ is H;

$R^5$ is H;

$R^{10}$ is H;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol;

$R^{14}$, $R^{15}$, $R^{16}$, and $R^{17}$ are each, independently, H, $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;

n is 1; and m is 0.

In some embodiments:

$R^2$ is —C(O)O—$R^{24}$;

$R^3$ is H;

$R^5$ is H;

$R^{10}$ is H;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, or $C_{1-4}$ alkylsulfonyl;

$R^{14}$, $R^{15}$, $R^{16}$, and $R^{17}$ are each, independently, H, $C_{1-4}$ alkoxy, $C_{1-8}$ alkyl, cyano, halogen, hydroxyl, or nitro;

n is 1; and m is 0.

In some embodiments:

$R^2$ is —C(O)O—$R^{24}$;

$R^3$ is H;

$R^5$ is H;

$R^{10}$ is H;

$R^{13}$ is $C_{1-4}$ alkylsulfinyl or $C_{1-4}$ alkylsulfonyl;

$R^{14}$ is halo;

$R^{15}$, $R^{16}$, and $R^{17}$ are each H;

$R^{24}$ is methyl, ethyl, or prop-1-yl, prop-2-yl;

n is 1; and m is 0.

In some embodiments:

$R^2$ is —C(O)O—$R^{24}$;

$R^3$ is H;

$R^5$ is H;

$R^{10}$ is H;

$R^{13}$ is methylsulfonyl;

$R^{14}$ is F;

$R^{15}$, $R^{16}$, and $R^{17}$ are each H;

$R^{24}$ is prop-2-yl;

n is 1; and m is 0.

Embodiments of Scheme I

The present invention provides, inter alia, processes for preparing compounds of Formula I:

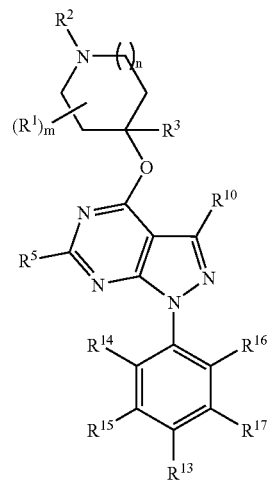

by reacting a compound of Formula II:

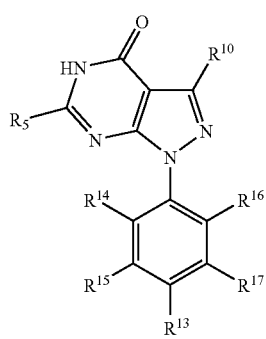

with a compound of Formula III:

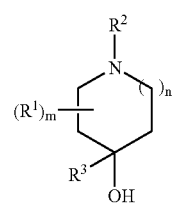

in the presence of a trisubstituted phosphine and a compound having the Formula A':

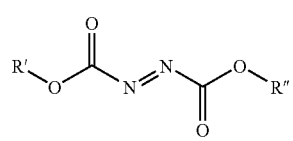

wherein R' and R" are each, independently, $C_{1-10}$ alkyl or $C_{3-7}$ cycloalkyl; to form the compound of Formula I.

The trisubstituted phosphine can be any suitable tertiary phosphine such as a phosphine having the formula $P(R)_3$, where each R is, independently, $C_{1-8}$ alkyl, aryl, cycloalkyl, heteroaryl, heterocyclic, arylalkyl, cycloalkylalkyl, heteroarylalkyl, or heterocyclicalkyl, each of which can be substituted by one or more halo, $C_{1-4}$ alkyl, $C_{1-4}$ haloalkyl, $C_{1-4}$ alkoxy, or $C_{1-4}$ haloalkoxy. In some embodiments, the trisubstituted phosphine is a triarylphosphine. In some embodiments, the trisubstituted phosphine is triphenylphosphine.

A suitable compound of Formula A' can be readily selected by the skilled artisan. In some embodiments, R' and R" are each, independently, $C_{1-10}$ alkyl. In further embodiments, R' and R" are each, independently, $C_{1-4}$ alkyl. In yet further embodiments, R' and R" are both prop-2-yl.

In some embodiments, the compound of Formula III is added to a mixture containing the compound of Formula II, the compound of Formula A', and the trisubstituted phosphine. Additional portions of phosphine and/or additional portions of the compound of Formula A' can be added after the initial reacting. In some embodiments, the total amount of phosphine is added in two or more portions. In some embodiments, the total amount of compound of Formula A' is added in two or more portions.

The reacting of II with III can be carried out at any suitable temperature. In some embodiments, the reacting is carried out at a temperature of about 35 to about 65, about 40 to about 60, or about 45 to about 55° C.

The reacting of II with III can also be optionally carried out in a solvent. Suitable solvents can be readily selected by the skilled artisan. Example solvents include polar to moderately polar solvents or high boiling solvents such as dimethylformamide (DMF), dimethylacetamide (DMA), toluene, acetonitrile, propionitrile, tetrahydrofuran (THF), N-methylpyrrolidine (NMP), or tertiary amines including cyclic amines. In some embodiments, the solvent includes a cyclic amine. In some embodiments, the cyclic amine is an N-alkylated morpholine such as 4-methylmorpholine.

The reacting of II with III can be carried out where the molar ratio of compound of Formula A' to compound of Formula II is about 2:1 to about 1:1, about 1.8:1 to about 1.2:1; or about 1.8:1 to about 1.5:1. In some embodiments, the molar ratio of trisubstituted phosphine to compound of Formula II is about about 2:1 to about 1:1, 1.8:1 to about 1.2:1, or about 1.8:1 to about 1.5:1. In further embodiments, the molar ratio of compound of Formula A' to trisubstituted phosphine is about 1:1. In yet further embodiments, the molar ratio of compound of Formula II to compound of Formula III is about 1:1.

In some embodiments, the reacting of II with III can result in the formation of a byproduct which is a structural isomer (e.g., has the same molecular weight) of the compound of Formula I. Accordingly, bulk samples of Formula I made by the processes described herein can contain a compound which is a structural isomer of the compound of Formula I. The amount of structural isomer byproduct in preparations of Formula I can be, for example, less than about 5%, less than about 3%, less than about 2%, less than about 1%, less than about 0.5%, less than about 0.2%, less than about 0.1%, less than about 0.05%, less than about 0.02%, or less than about 0.01% by weight in the bulk sample.

The present invention further provides processes for preparing a compound of Formula II by reacting a compound of Formula IV:

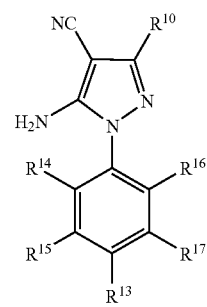

IV with $R^5C_2H$ to form the compound of Formula II.

The reacting of IV with acid $R^5CO_2H$ can be optionally carried out in the presence of any suitable solvent readily selected by the skilled artisan. In some embodiments, the solvent is a polar solvent and/or a high boiling solvent (e.g., boils above 100° C). Example suitable solvents include an aqueous solvent (water or water mixture containing greater than about 5 wt % water), dimethylsulfoxide (DMSO), dimethylformamide (DMF), dimethylacetamide (DMA), N-methylpyrrolidine (NMP), propionitrile, and the like. In some embodiments, the solvent is an aqueous solvent such as water.

The reacting of IV with acid $R^5CO_2H$ can be optionally carried out in the presence of a strong acid, for example, sulfuric acid. In some embodiments, the strong acid is present from about 0.5 equivalents to about 3 equivalents compared to a compound of Formula IV. In further embodiments, the strong acid is present from about 1 equivalent to about 2.5 equivalents compared to a compound of Formula IV. In yet further embodiments, the strong acid is present in about 2 equivalents compared to a compound of Formula IV. In certain embodiments, the presence of the strong acid reduces the reaction time by a factor of about 7 to about 4 compared to the reaction time in the absence of strong acid.

The reacting of IV with acid $R^5CO_2H$ can be carried out at any suitable temperature. For example, the reaction can be carried out at elevated temperature for at least a portion of the reacting. In some embodiments, the temperature is reflux temperature. In further embodiments, the reaction is carried out at a temperature of about 80 to about 120° C. In yet further embodiments, the reaction is carried out at a temperature of about 80 to about 120° C. and then the resulting mixture is cooled to about −20 to about 20° C. The cooling process can be relatively rapid, cooling the mixture in less than about 2, less than about 1, or less than about 0.5 hours.

While not wishing to be bound by theory, it is believed that the relatively rapid cooling substantially prevents or inhibits the hydrolysis of the bicyclic product II, which is a competing reaction that appears to be favored at intermediate temperatures (e.g., 70-80° C). An example byproduct of hydrolysis of II is shown in Formula IIb:

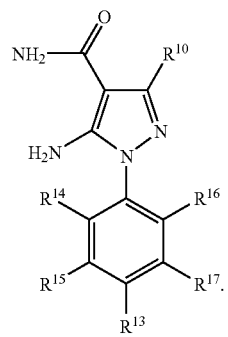

IIb

In some embodiments, bulk samples of the compound of Formula II made by the processes described herein can contain a detectable amount of compound of Formula IIb. The amount of compound of Formula IIb in preparations of Formula II can be, for example, less than about 5%, less than about 3%, less than about 2%, less than about 1%, less than about 0.5%, less than about 0.2%, less than about 0.1%, less than about 0.05%, less than about 0.02%, or less than about 0.01% by weight of the bulk sample.

Because the byproduct of Formula IIb can be carried over to preparations of Formula I, bulk samples of Formula I made by the processes described herein can contain a detectable amount of compound of Formula IIb. The amount of compound of Formula IIb in preparations of Formula I can be, for example, less than about 5%, less than about 3%, less than about 2%, less than about 1%, less than about 0.5%, less than about 0.2%, less than about 0.1%, less than about 0.05%, less than about 0.02%, or less than about 0.01% by weight.

The compound of Formula IIb and other byproducts can be detected and quantified by routine methods including, for example, proton nuclear magnetic resonance, high performance liquid chromatography, mass spectrometry, and the like. The amount of compound of Formula IIb and other byproducts in bulk samples prepared according to the processes herein can be reduced or substantially eliminated by routine methods such as recrystallization or chromatography techniques.

The term "bulk sample" is used herein consistently with its meaning in the art which, for example, refers to an amount of product prepared according to a given process or procedure. Bulk samples can be any size, but typically range from about 1 mg on upward to several thousands of kilograms or more.

The reacting of IV with acid $R^5CO_2H$ can further be carried out wherein the $R^5CO_2H$ is provided in molar excess relative to the compound of Formula IV. In some embodiments, the molar ratio of acid $R^5CO_2H$ to compound of Formula IV is about 100:1 to about 2:1; about 70:1 to about 10:1; about 50:1 to about 30:1, about 45:1 to about 35:1, or about 40:1. In some embodiments, the acid $R^5CO_2H$ is added in two or more portions. In some instances when, for example, the reaction is conducted at elevated temperature, a volatile acid or ester thereof may distill away. Thus, additional amounts of acid can be added periodically to maintain a molar excess with respect to the compound of Formula IV.

In the reacting of $R^5CO_2H$ with the compound of Formula IV, the reaction can be carried out for a duration until product of Formula II is detected. In some embodiments, the reaction is carried out until greater than about 50, greater than about 75, greater than about 80, greater than about 90, greater than about 95, greater than about 97, greater than about 98 or greater than about 99, greater than about 99.5% (e.g., mol %) of the compound of Formula IV is converted to the compound of Formula II. The conversion can be quantitated and/or monitored by any suitable method routine in the art such as by HPLC.

The present invention further provides a process for preparing a compound of Formula IV by reacting a compound of Formula V:

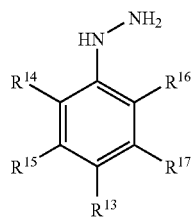

with a compound of Formula VI:

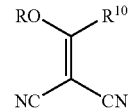

thereby forming the compound of Formula IV.

The reacting of the compound of Formula V with the malonitrile of Formula VI can be optionally carried out in a solvent. Any suitable solvent can be selected by the skilled artisan. In some embodiments, the solvent is an alcohol such as methanol, ethanol, n-propanol, isopropanol, n-butanol, and the like. In some embodiments, the solvent is methanol.

The reacting of the compound of Formula V with the malonitrile of Formula VI can be optionally carried out in the absence of a base. Example bases which can be absent include alkoxides such as methoxide or ethoxide (e.g., provided as alkali metal or other salts thereof).

Further, the reacting of the compound of Formula V with the malonitrile of Formula VI can be carried out where the molar ratio of the compound of Formula V to the malonitrile of Formula VI is about 1:2 to about 1:1, about 1:1.5 to about 1:1, about 1:1.2 to about 1:1, or about 1:1.1.

Reaction between the compound of Formula V and the malonitrile of Formula VI can be carried out at any suitable temperature readily selected by the art skilled. For example, the reaction can be carried out at a temperature less than 0° C. such as at about −20 to about 10 or about −10 to about 0° C.

The compounds of Formulas III, IV, and V can be prepared according to routine methods in the art. Example preparations of these compounds are provided in U.S. Ser. No. 10/890,549, which is incorporated herein by reference in its entirety.

Embodiments of Scheme II

The present invention further provides processes for preparing compounds of Formula I by reacting a compound of Formula IIa:

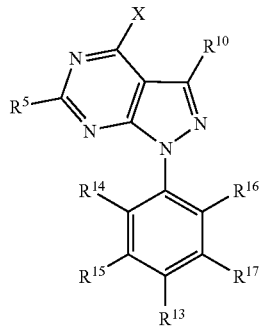

with a compound of Formula III in the presence of a base, to form the compound of Formula I.

The base can be any suitable base readily selected by the skilled artisan. For example, the base can be an alkoxide salt. Any suitable alkoxide salt can be used such as, for example, alkali metal or other salts of methoxide, ethoxide, propoxide, isopropoxide, n-butoxide, isobutoxide, t-butoxide, and the like. In some embodiments, the alkoxide salt is an alkali metal alkoxide. In some embodiments, the alkoxide salt is a t-butoxide salt. In some embodiments, the alkoxide salt is sodium t-butoxide. Other suitable bases include, for example, alkali metal hydrides (e.g., NaH), alkali metal amides (e.g., sodamide), alkali metal carbonates (e.g., $Na_2CO_3$, $K_2CO_3$, etc.), and the like.

The reacting of the compound of Formula IIa with the compound of Formula III can be optionally carried out in a solvent. A suitable solvent can be readily selected by the skilled artisan. For example, the solvent can be an aromatic solvent such as benzene, toluene, nitrobenzene, chlorobenzene, and the like. In some embodiments, the solvent includes toluene. Other suitable solvents include polar to moderately polar solvents or high boiling solvents such as dimethylformamide (DMF), dimethylacetamide (DMA), toluene, acetonitrile, propionitrile, tetrahydrofuran (THF), N-methylpyrrolidine (NMP), or tertiary amines including cyclic amines such as an N-alkylated morpholine (e.g., 4-methylmorpholine).

Further, the reacting of the compound of Formula IIa with the compound of Formula III can be optionally carried out for at least a portion of the time at a temperature below about 40, below about 30, below about 20, or below about 15° C.

In some embodiments, the molar ratio of the compound of Formula III to the compound of Formula IIa is about 2:1 to about 1:1, about 1.5:1 to about 1:1 or about 1.2:1. In further embodiments, the molar ratio of alkoxide salt to the compound of Formula IIa is about 2:1 to about 1:1, about 1.5:1 to about 1:1, about 1.3:1 to about 1:1, or about 1.3:1.

The present invention further provides processes for preparing compounds of Formula IIa by reacting a compound of Formula II with a halogenating reagent to form the compound of Formula IIa.

The halogenating reagent can be any reagent capable of halogenating the compound of Formula IIa. Any of numerous halogenating reagents are known in the art. In some embodiments, the halogenating reagent is a brominating or chlorinating reagent. Some example brominating reagents include, for example, $Br_2$, N-bromosuccinimide (NBS), 1,3-dibromo-5,5-dimethylhydantoin, pyridinium tribromide ($pyrHBr_3$), $POBr_3$, and the like. Example chlorinating reagents include N-chlorosuccinimide, $POCl_3$, and the like. In some embodiments, the halogenating reagent is $POX_3$ where X is halo such as Cl or Br. In some embodiments, the halogenating reagent is $POCl_3$.

The reacting of a compound of Formula II with a halogenating reagent can be optionally carried out in the presence of a catalyst. In some embodiments, the catalyst includes a di-substituted amide such as a compound having the Formula $R^{cat}C(O)N(R')(R'')$ wherein $R^{cat}$ is H, $C_{1-8}$ alkyl, aryl, heteroaryl, and the like; and each R' and R'' is, independently, $C_{1-8}$ alkyl. In further embodiments, the di-substituted amide is dimethylformamide (DMF) or dimethylacetamide (DMA). In some embodiments, the di-substituted amide is DMF.

The reacting of a compound of Formula II with a halogenating reagent can be optionally carried out at an elevated temperature. For example, the reaction mixture can be heated to reflux. In some embodiments, the temperature for at least a portion of the reaction time can be about 80 to about 140° C.

In some embodiments, the halogenating reagent can be provided in molar excess relative to the amount of compound of Formula II. For example, the molar ratio of halogenating reagent to the amount of compound of Formula II can be about 50:1 to about 2:1, about 25:1 to about 2:1, or about 15:1 to about 7:1. In some embodiments, the molar ratio of compound of Formula II to amount of catalyst is about 2:1 to about 1:1, about 1.5:1 to about 1:1, or about 1.3:1 to about 1.2:1. In some embodiments, the catalyst is added to the reaction mixture in two or more portions. In further embodiments, the portions of catalyst are substantially equal in amount.

Definitions

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

The term "$C_{i-j}$" denotes the number of carbon atoms in the moiety to which the term refers. For example, $C_{1-8}$ alkyl (where i is 1 and j is 8) refers to an alkyl group having 1 ($C_1$), 2 ($C_2$), 3 ($C_3$), 4 ($C_4$), 5 ($C_5$), 6 ($C_6$), 7 ($C_7$), or 8 ($C_8$) carbon atoms.

The term "acyl" denotes a carbonyl (C=O) substituted by an alkyl radical, wherein the definition of alkyl has the same definition as described herein. Some examples include, but are not limited to, acetyl, propionyl, n-butanoyl, iso-butanoyl, sec-butanoyl, t-butanoyl (i.e., pivaloyl), pentanoyl and the like.

The term "acyloxy" denotes —O— substituted by an acyl radical, wherein acyl has the same definition has described herein. Some examples include but are not limited to acetyloxy, propionyloxy, butanoyloxy, iso-butanoyloxy, sec-butanoyloxy, t-butanoyloxy and the like.

The term "acylsulfonamide" refers to a sulfonamide substituted by acyl on the sulfonamide N-atom, wherein the definitions for acyl and sulfonamide have the same meaning as described herein, and an acylsulfonamide can be represented by the following formula:

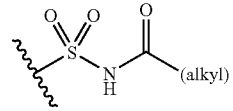

Some embodiments of the present invention include $C_{1-5}$ acylsulfonamide, $C_{1-4}$ acylsulfonamide, $C_{1-3}$ acylsulfonamide, or $C_{1-2}$ acylsulfonamide. Examples of acylsulfonamides include, but are not limited to, acetylsulfamoyl [—S(=O)$_2$NHC(=O)Me], propionylsulfamoyl [—S(=O)$_2$NHC(=O)Et], isobutyrylsulfamoyl, butyrylsulfamoyl, 2-methyl-butyrylsulfamoyl, 3-methyl-butyrylsulfamoyl, 2,2-dimethyl-propionylsulfamoyl, pentanoylsulfamoyl, 2-methyl-pentanoylsulfamoyl, 3-methyl-pentanoylsulfamoyl, 4-methyl-pentanoylsulfamoyl, and the like.

The term "alkenyl" denotes an alkyl radical containing having at least one carbon-carbon double bond. In some embodiments, the alkenyl group is $C_{2-6}$ alkenyl, $C_{2-5}$ alkenyl, $C_{2-4}$ alkenyl, $C_{2-3}$ alkenyl or $C_2$ alkenyl. Both E and Z isomers are embraced by the term "alkenyl." Furthermore, the term "alkenyl" includes groups with 1, 2, 3, 4 or more double bonds. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "alkyl" denotes a straight or branched hydrocarbon radical. In some embodiments, the alkyl group contains 1 to 8 carbons, 1 to 7 carbons, 1 to 6 carbons, 1 to 5 carbons, 1 to 4 carbons, 1 to 3 carbons, 1 or 2 carbons. Examples of alkyl groups include, but are not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)

CH$_2$CH$_2$CH$_3$], 2-methylbutyl [i.e., —CH$_2$CH(CH$_3$) CH$_2$CH$_3$], n-hexyl and the like.

The term "alkylcarboxamido" or "alkylcarboxamide" denotes a single alkyl group attached to the nitrogen or carbon of an amide group, wherein alkyl has the same definition as found herein. The alkylcarboxamide may be represented by the following:

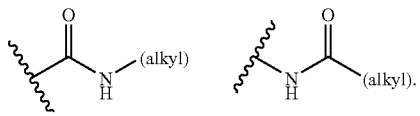

Examples include, but are not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "alkylene" refers to a divalent alkyl group. In some embodiments, alkylene refers to, for example, —CH$_2$—, —CH$_2$CH$_2$—, —CH$_2$CH$_2$CH$_2$—, and the like. In some embodiments, alkylene refers to —CH—, —CHCH$_2$—, —CHCH$_2$CH$_2$—, and the like wherein these examples relate generally to "A".

The term "alkylsulfinyl" denotes —S(O)— substituted by alkyl, wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "alkylsulfonamide" refers to the groups

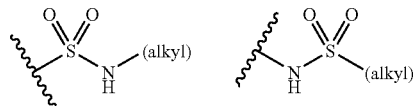

wherein alkyl has the same definition as described herein.

The term "alkylsulfonyl" denotes —S(O)$_2$— substituted by alkyl, wherein the alkyl radical has the same definition as described herein. Examples include, but are not limited to, methylsulfonyl, ethylsulfonyl, n-propylsulfonyl, iso-propylsulfonyl, n-butylsulfonyl, sec-butylsulfonyl, iso-butylsulfonyl, t-butyl, and the like.

The term "alkylthio" denotes —S— substituted by alkyl, wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "alkylthiocarboxamide" denotes a thioamide of the following formulae:

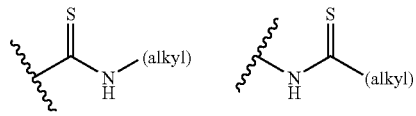

wherein alkyl has the same definition as described herein.

The term "alkylthioureyl" denotes the group of the formula: —NC(S)N— wherein one or both of the nitrogens are substituted with the same or different alkyl groups, and alkyl has the same definition as described herein. Examples of an alkylthioureyl include, but are not limited to, CH$_3$NHC(S)NH—, NH$_2$C(S)NCH$_3$—, (CH$_3$)$_2$N(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "alkylureyl" denotes the group of the formula: —NC(O)N— wherein one are both of the nitrogens are substituted with the same or different alkyl group, wherein alkyl has the same definition as described herein. Examples of an alkylureyl include, but not limited to, CH$_3$NHC(O)NH—, NH$_2$C(O)NCH$_3$—, (CH$_3$)$_2$N(O)NH—, (CH$_3$)$_2$N(O)NH—, (CH$_3$)$_2$N(O)NCH$_3$—, CH$_3$CH$_2$NHC(O)NH—, CH$_3$CH$_2$NHC(O)NCH$_3$—, and the like.

The term "alkynyl" denotes an alkyl group having at least one carbon-carbon triple bond. In some embodiments, the alkynyl group has 2 to 8 carbons, 2 to 7 carbons, 2 to 6 carbons, 2 to 5 carbons, 2 to 4 carbons, 2 to 3 carbons, or 2 carbons. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Additionally, an alkynyl group can have 1, 2, 3, 4 or more triple bonds, forming for example, di- and tri-ynes.

The term "amino" denotes the group —NH$_2$.

The term "alkylamino" denotes amino substituted by alkyl, wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like.

The term "aryl" denotes monocyclic or polycyclic aromatic hydrocarbons such as, for example, phenyl, naphthyl, anthracenyl, phenanthrenyl, indanyl, indenyl, and the like. In some embodiments, aryl groups have from 6 to about 20 carbon atoms.

The term "arylalkyl" denotes alkyl substituted with an aryl group. Examples of an "arylalkyl" include benzyl, phenethylene and the like.

The term "arylcarboxamido" denotes an amide group substituted by an aryl group on the N-atom, wherein aryl has the same definition as found herein. An example is N-phenylcarboxamide.

The term "arylureyl" denotes the group —NC(O)N— where one of the nitrogens are substituted with an aryl.

The term "benzyl" denotes the group —CH$_2$C$_6$H$_5$.

The term "carbamimidoyl" refers to a group of the following chemical formula:

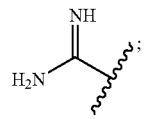

and in some embodiments, one or both hydrogens are replaced with another group. For example, one hydrogen can be replaced with a hydroxyl group to give a N-hydroxycarbamimidoyl group, or one hydrogen can be replaced with an alkyl group to give N-methylcarbamimidoyl, N-ethylcarbamimidoyl, N-propylcarbamimidoyl, N-butylcarbamimidoyl, and the like.

The term "carboalkoxy" refers to an alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "carboxamide" refers to the group —$CONH_2$.

The term "carboxy" or "carboxyl" denotes the group —$CO_2H$; also referred to as a carboxylic acid group.

The term "cyano" denotes the group —CN.

The term "cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "cycloalkyl" denotes a saturated, cyclic hydrocarbon containing, for example, 3 to 14, 1 to 10, 3 to 8, 3 to 7, 3 to 6, 3 to 5, or 3 to 4 carbons. Examples include cyclopropyl, cyclobutyl, cyclopentyl, cyclopenyl, cyclohexyl, cycloheptyl and the like.

The term "cycloalkylalkyl" denotes an alkyl group substituted by a cycloalkyl group.

The term "cycloalkylene" refers to a divalent cycloalkyl radical. In some embodiments, the two bonding groups are on the same carbon, for example:

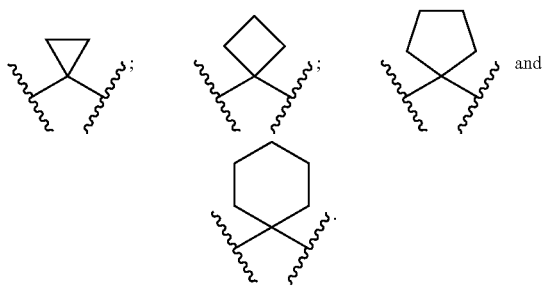

In some embodiments, the two bonding groups are on different carbons.

The term "diacylamino" denotes an amino group substituted with two acyl groups, wherein the acyl groups may be the same or different, such as:

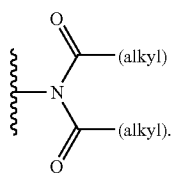

Examples of diacylamino groups include, but limited to, diacetylamino, dipropionylamino, acetylpropionylamino and the like.

The term "dialkylamino" denotes an amino group substituted with two of the same or different alkyl radicals, wherein alkyl has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like.

The term "dialkylcarboxamido" or "dialkylcarboxamide" denotes an amide substituted by two alkyl radicals, that are the same or different. Dialkylcarboxamidos can be represented by the following groups:

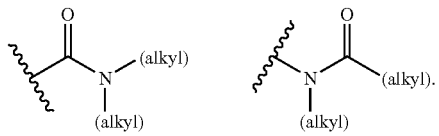

Examples of dialkylcarboxamides include, but are not limited to, N,N-dimethylcarboxamide, N-methyl-N-ethylcarboxamide, N,N-diethylcarboxamide, N-methyl-N-isopropylcarboxamide, and the like.

The term "dialkylsulfonamide" refers to one of the following groups shown below:

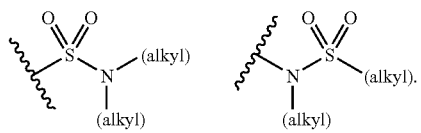

Examples include, but are not limited to, methyl, ethyl, n-propyl, isopropyl, and the like.

The term "dialkylthiocarboxamido" or "dialkylthiocarboxamide" denotes a thioamide substituted by two alkyl radicals, that are the same or different, wherein alkyl has the same definition as described herein. Example dialkylthiocarboxamido groups can be represented by the following groups:

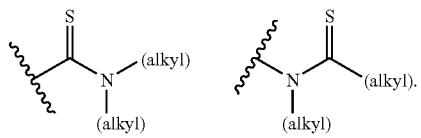

Examples of dialkylthiocarboxamides include, but are not limited to, N,N-dimethylthiocarboxamide, N-methyl-N-ethylthiocarboxamide and the like.

The term "dialkylsulfonylamino" refers to an amino group substituted with two alkylsulfonyl groups as defined herein.

The term "ethynylene" refers to —C≡C—.

The term "formyl" refers to the group —CHO.

The term "guanidine" refers to a group of the following chemical formula:

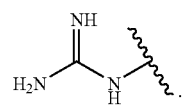

The term "haloalkoxy" denotes —O— substituted by haloalkyl. Examples include, but are not limited to, difluoromethoxy, trifluoromethoxy, 2,2,2-trifluoroethoxy, pentafluoroethoxy, and the like.

The term "haloalkyl" denotes an alkyl group, as defined herein, wherein the alkyl is substituted with one or more halogens. Examples of haloalkyl groups include, but are not limited to, fluoromethyl, difluoromethyl, trifluoromethyl, chlorodifluoromethyl, 2,2,2-trifluoroethyl, pentafluoroethyl and the like.

The term "haloalkylcarboxamide" denotes an alkylcarboxamide group, defined herein, substituted with one or more halogens.

The term "haloalkylsulfinyl" denotes sulfoxide —S(O)— substituted by a haloalkyl radical, wherein the haloalkyl radical has the same definition as described herein. Examples include, but are not limited to, trifluoromethylsulfinyl, 2,2,2-trifluoroethylsulfinyl, 2,2-difluoroethylsulfinyl and the like.

The term "haloalkylsulfonyl" denotes —S(O)$_2$— substituted by a haloalkyl radical, wherein haloalkyl has the same definition as described herein. Examples include, but not limited to, trifluoromethylsulfonyl, 2,2,2-trifluoroethylsulfonyl, 2,2-difluoroethylsulfonyl and the like.

The term "haloalkylthio" denotes —S— substituted by a haloalkyl radical, wherein the haloalkyl has the same meaning as described herein. Examples include, but not limited to, trifluoromethylthio (i.e., $CF_3S$—), 1,1-difluoroethylthio, 2,2,2-trifluoroethylthio and the like.

The term "halogen" or "halo" denotes to a fluoro, chloro, bromo or iodo group.

The term "heteroalkylene" refers to alkylene interrupted or appended by a heteroatom-containing group selected from O, S, S(O), S(O)$_2$ and NH. Some examples include, but not limited to, the groups of the following formulae:

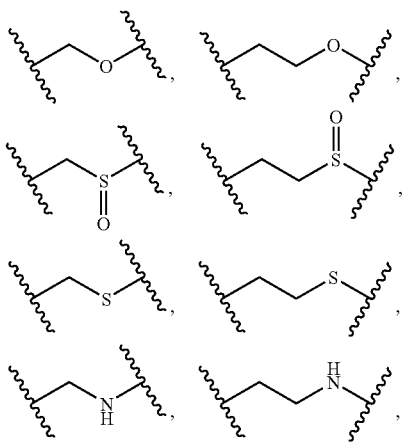

and the like.

The term "heteroaryl" denotes an aromatic ring system that may be a single ring, two fused rings or three fused rings wherein at least one ring carbon is a heteroatom selected from, but not limited to, the group consisting of O, S and N, wherein the N can be optionally substituted with H, O, $C_{1-4}$ acyl or $C_{1-4}$ alkyl. Examples of heteroaryl groups include, but are not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroatom is O, S, NH, examples include, but not limited to, pyrrole, indole, and the like.

The term "heteroarylalkyl" denotes an alkyl group substituted by a heteroaryl group.

The term "heterocyclic" denotes a non-aromatic, cyclic hydrocarbon (i.e., cycloalkyl or cycloalkenyl as defined herein) wherein one or more (e.g., one, two or three) ring carbons are replaced by a heteroatom selected from, but not limited to, the group consisting of O, S, N, wherein the N can be optionally substituted with H, O, $C_{1-4}$ acyl or $C_{1-4}$ alkyl, and ring carbon atoms are optionally substituted with oxo or a sulfido thus forming a carbonyl or thiocarbonyl group. The heterocyclic group can be a 3-, 4-, 5-, 6- or 7-membered ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term, "heterocyclicalkyl" denotes an alkyl group substituted by a heterocyclic group.

The term "heterocyclic-carbonyl" denotes a carbonyl group substituted by a heterocyclic group, as defined herein. In some embodiments, a ring nitrogen of the heterocyclic group is bonded to the carbonyl group forming an amide. Examples include, but are not limited to,

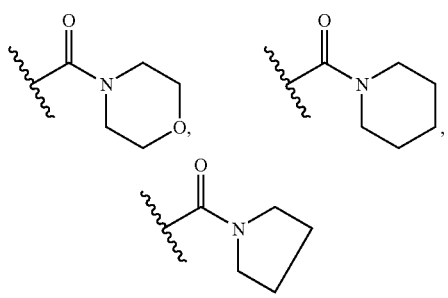

and the like.

In some embodiments, a ring carbon is bonded to the carbonyl group forming a ketone group. Examples include, but are not limited to,

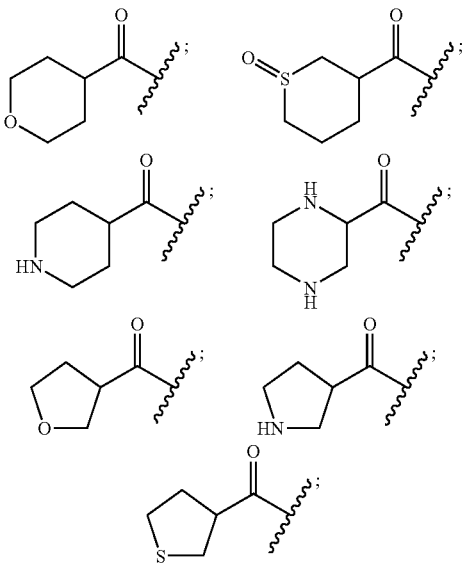

and the like.

The term "heterocyclic-oxy" refers —O— substituted by a heterocyclic group, as defined herein. Examples include the following:

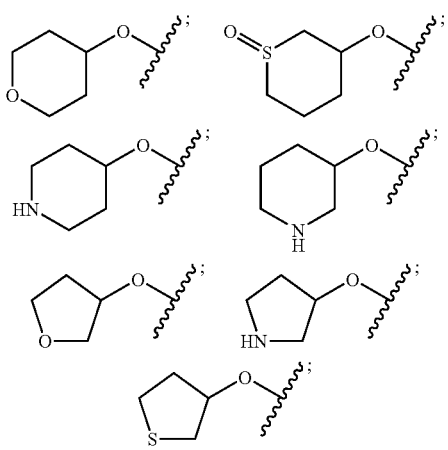

and the like.

The term "heterocyclicsulfonyl" denotes SO$_2$ substituted with a heterocyclic group having a ring nitrogen, where the ring nitrogen is bonded directly to an SO$_2$ group forming an sulfonamide. Examples include, but not limited to,

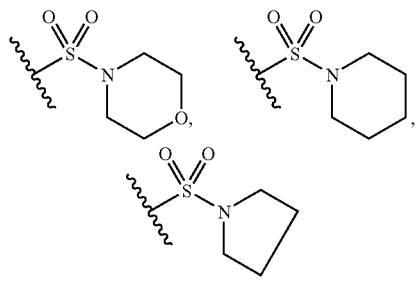

and the like.

The term "hydroxyl" refers to the group —OH.

The term "hydroxylamino" refers to the group —NHOH.

The term "nitro" refers to the group —NO$_2$.

The term "oxo-cycloalkyl" refers to cycloalkyl, as defined herein, wherein one of the ring carbons is replaced with a carbonyl. Examples of oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

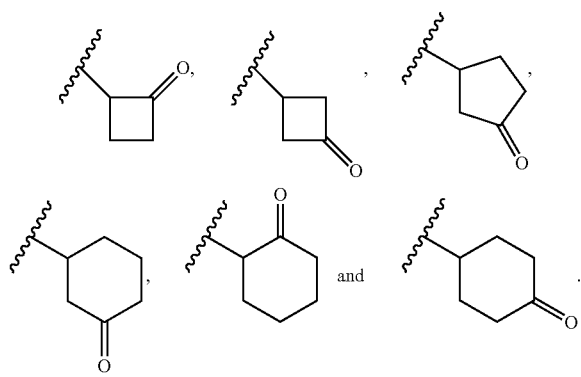

The term "perfluoroalkyl" denotes the group of the formula —C$_n$F$_{2+1}$. Examples of perfluoroalkyls include CF$_3$, CF$_2$CF$_3$, CF$_2$CF$_2$CF$_3$, CF(CF$_3$)$_2$, CF$_2$CF$_2$CF$_2$CF$_3$, CF$_2$CF(CF$_3$)$_2$, CF(CF$_3$)CF$_2$CF$_3$ and the like.

The term "phenoxy" refers to the group C$_6$H$_5$O—.

The term "phenyl" refers to the group C$_6$H$_5$—.

The term "phosphonooxy" refers to a group with the following chemical structure:

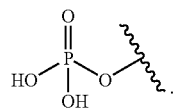

The term "sulfonamide" refers to the group —SO$_2$NH$_2$.

The term "sulfonic acid" refers to the group —SO$_3$H.

The term "tetrazolyl" refers to the five membered heteroaryl of the following formulae:

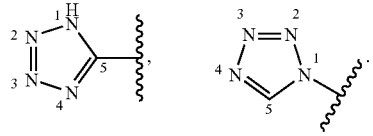

In some embodiments, the tetrazolyl group is further substituted at either the 1 or 5 position, resepectively, with a group selected from the group consisting of alkyl, haloalkyl and alkoxy.

The term "thiol" denotes the group —SH.

As used herein, the term "reacting" is used as known in the art and generally refers to the bringing together of chemical reagents in such a manner so as to allow their interaction at the molecular level to achieve a chemical or physical transformation of at least one chemical reagent.

As used herein, the term "substituted" refers to the replacement of a hydrogen moiety with a non-hydrogen moiety in a molecule or group.

For compounds in which a variable appears more than once, each variable can be a different moiety selected from the Markush group defining the variable. For example, where a structure is described having two R groups that are simultaneously present on the same compound; the two R groups can represent different moieties selected from the Markush group defined for R. In another example, when an optionally multiple substituent is designated in the form:

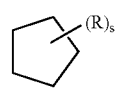

then it is understood that substituent R can occur s number of times on the ring, and R can be a different moiety at each occurrence.

As used herein, the term "leaving group" refers to a moiety that can be displaced by another moiety, such as by nucleophilic attack, during a chemical reaction. Leaving groups are well known in the art and include, for example, halogen including chloro, bromo, iodo, and the like.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, et al., *Protective Groups in Organic Synthesis*, 3rd. Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol. monomethyl ether, diethylene glycol monoethyl ether, cyclohexanol, benzyl alcohol, phenol, or glycerol.

Suitable aprotic solvents can include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide can also be used as a solvent.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 25° C) and "reduced temperature" refers to temperatures below room temperature.

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as α-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds according to the invention can also include all isotopes of atoms occurring in the intermediates or final compounds. Isotopes include those atoms having the same atomic number but different mass numbers. For example, isotopes of hydrogen include tritium and deuterium.

Compounds according to the invention can also include tautomeric forms, such as keto-enol tautomers. Tautomeric forms can be in equilibrium or sterically locked into one form by appropriate substitution.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 5-Amino-1-(2-fluoro-4-methanesulfonyl-phenyl)-1H-pyrazole-4-carbonitrile (3)

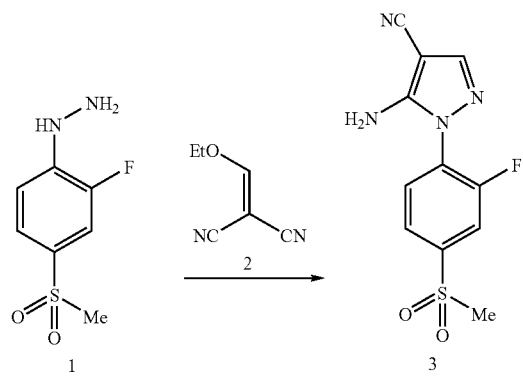

To a stirred suspension of 2-fluoro-4-methylsulfonylphenyl hydrazine (1) (4.0336 Kg; 1 eq) (commercially available from, e.g., Peakdale Molecular, Ltd.) in methanol (12.7723 Kg) was added a suspension of ethoxymethylene malononitrile (2.6564 Kg, 1.101 equivalents) in methanol (11.212 Kg) at a rate sufficiently slow to maintain the reaction mixture at −10° to 0° C. with reactor jacket cooling. After the addition had been completed, the reaction mixture was stirred for 1 hour at −6° C. and then heated to reflux for 5 hours, at which time the reaction mixture gave a pyrazole (3): hydrazine (1) HPLC peak area ratio of 105:1. Solvent (20.5153 Kg) was then distilled off the reaction mixture at atmospheric pressure, leaving a residue having less than 20% of the original volume. The resulting mixture was used directly in the next step.

Example 2

Example 2A

Preparation of 1-(2-fluoro-4-methanesulfonyl-phenyl)-1,5-dihydro-pyrazolo[3,4-d]pyrimidin-4-one (4)

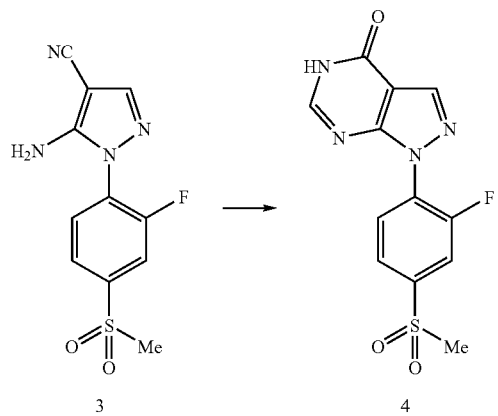

To the concentrated reaction mixture from Example 1 containing pyrazole (3) was added formic acid (36.3924 Kg, 40.0 equivalents) and then water (2.832 Kg) at a rate sufficiently slow to maintain the reaction mixture at 25° to 35° C. with reactor jacket cooling. After an additional 6.345 Kg of solvent had been distilled off the stirred reaction mixture at atmospheric pressure, more formic acid (1.8245 Kg) and then more water (0.564 Kg) were added at a rate sufficiently slow to maintain the reaction mixture at 25° to 35° C. with reactor jacket cooling. A small amount of remaining volatiles were then distilled off the stirred reaction mixture at atmospheric pressure until a reflux temperature of 100° C. was achieved. After six hours of reflux, the reaction mixture gave a product (4):pyrazole (3) HPLC peak area ratio of 670 :1. The only other detectable component had an HPLC peak area 0.41% of that for product (4). After the reaction mixture is cooled from reflux to 0° C. in 70 minutes, water (10.0 Kg) is added, and the precipitated product is filtered, washed with 20° C. water (about 40 Kg) until the pH of the wash filtrate is at least 5, and then dried to constant weight at 45° C., ≦40 torr to provide product (4).

Example 2B

Preparation of 1-(2-fluoro-4-methanesulfonyl-phenyl)-1,5-dihydro-pyrazolo[3,4-d]pyrimidin-4-one (4)

A similar preparation of (4) was carried out where the refluxed reaction mixture was held at a holding temperature of about 70-80° C. overnight after achieving complete conversion to (4) (>99%). In this preparation, an impurity identified as 5-amino-1-(2-fluoro-4-methanesulfonyl-phenyl)-1H-pyrazole-4-carboxylic acid amide was detected at about 30% (HPLC % peak area). This impure preparation of 4 containing 4a (5.01 g) was purified by additional refluxing in formic acid (25 mL) for about 7 h. After each hour of refluxing, a sample was collected. Each sample revealed the presence of 4a as well as about an equal amount of 1-(2-fluoro-4-methanesulfonyl-phenyl)-5-formylamino-1H-pyrazole-4-carboxylic acid amide; however the total amount of impurity decreased during the course of the refluxing until essentially complete conversion was achieved after 7 hours.

Example 2C

Preparation of 1-(2-Fluoro-4-methanesulfonyl-phenyl)-1,7-dihydro-pyrazolo[3,4-d]pyrimidin-4-one (4)

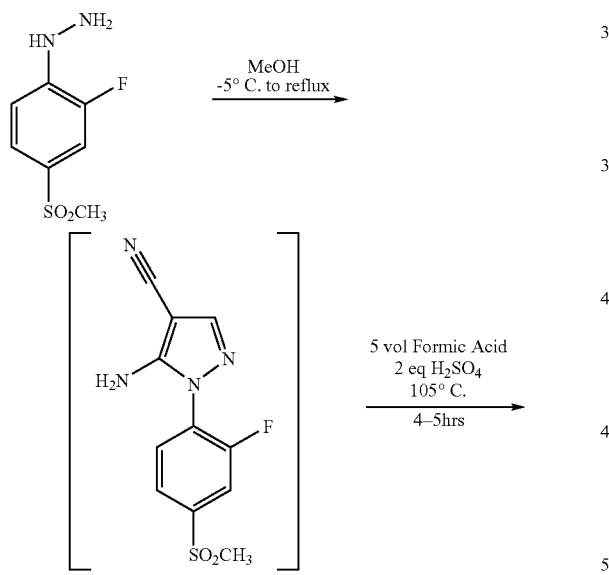

To a one liter, bottom discharge jacketed glass reactor equipped with overhead agitation, reflux condenser and nitrogen blanket bubbler was added (2-fluoro-4-methanesulfonyl-phenyl)-hydrazine (50.0 g, 0.244 mol) with the aid of methanol (200 mL, 4 vol Eq.). The resulting reaction mixture was a light slurry and subsequently cooled to −5° C. In a separate vessel was made a suspension of ethoxymethylene malononitrile (EMM) (32.9 g, 0.270 mol) in methanol (205 mL, 4.1 Vol. Eq.). The resulting EMM/MeOH suspension was added dropwise to the reaction containing (2-fluoro-4-methanesulfonyl-phenyl)-hydrazine at a rate that maintains the reaction temperature at about −5C. The reaction mixture was then held at about −5° C. until all of the starting material ((2-fluoro-4-methanesulfonyl-phenyl)-hydrazine) was consumed, typically about 2-4 hrs. The resulting reaction mixture was heated to reflux for about 2-4 hours until complete conversion to intermediate 5-amino-1-(2-fluoro-4-methanesulfonyl-phenyl)-1H-pyrazole-4-carbonitrile (shown in bracket above) is greater then 99%. The reaction mixture was then stripped to near dryness under full house vacuum (<20 torr) with a maximum jacket temperature of 65° C. to afford a soft orange solid. The solid was then dissolved in formic acid (250 mL, 5 Vol. Eq.) and sulfuric acid (24.0 g, 0.245 mol) yielding a dark red transparent solution. The solution was heated to reflux (105-110° C.) and held until reaction was complete (about 4-5 hrs). The addition of sulfuric acid showed nearly complete conversion of intermediate 5-amino-1-(2-fluoro-4-methanesulfonyl-phenyl)-1H-pyrazole-4-carbonitrile to another intermediate 5-amino-1-(2-fluoro-4-methanesulfonyl-phenyl)-1H-pyrazole-4-carboxylic acid amide as well as the title compound in one hour with no unknown intermediate (m/z 327 (m+H)+ present. The disappearance of 5-amino-1-(2-fluoro-4-methanesulfonyl-phenyl)-1H-pyrazole-4-carboxylic acid amide and appearance of the title compound was then followed until the reaction was complete. After the reaction was complete, the reaction mixture was cooled to 65° C. and water (100 mL, 2 Vol Eq.) was slowly added to aid in product precipitation. Water was added slowly as it was slightly exothermic, also rapid addition will make reaction mixture very thick. Slower addition maintains reaction stirrability. Higher temperature additions may alleviate any stirring problems. The reaction was allowed to stir for 1-2 hrs at 20-25° C. and was filtered. Filtration was quite rapid. Cooling to 0-5° C. may aid in additional yield. The cake was washed with water (2×100 mL) followed by sodium bicarbonate (aqueous 5%, 1×150 mL) to neutralize residual acid. Cake was again washed with water (1×150 mL) and dried overnight, 65° C., full house vacuum (<20 torr) to afford 67.4 grams of dried light tan/white of the title compound @ about 100.0% HPLC purity. The overall molar yield was 89.2%.

Example 3

Preparation of 4-Hydroxy-Piperidine-1-Carboxylic Acid Isopropyl Ester (5)

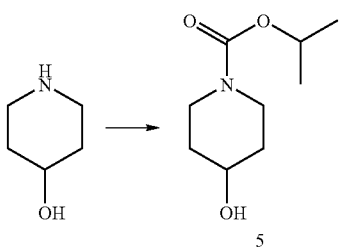

5

To a stirred mixture of 4-hydroxypiperidine (53.8 g, 1.000 eq), triethylamine (71.8 g, 1.334 equivalents), and ethyl acetate (498.8 g) was added neat isopropyl chloroformate (78.0 g, 1.1966 equivalents) at a rate sufficiently slow to maintain the reaction mixture temperature at 10°-17° C. with reactor jacket cooling. After the addition had been completed, the reaction mixture was stirred at 20° C. for 18 hours. Then water (100 g) was added, and the resulting mixture was stirred for 15 minutes before the phases were separated. The organic phase was washed with two 100-gram-portions of 20 wt % aqueous NaCl by stirring for 15 min at 150 rpm before separating the aqueous wash. After a final wash with water (100 g), the organic phase was concentrated by distillation on a rotary evaporator at reduced pressure to provide product (2) (91.1 g, 92.0% yield) as light amber oil of 96.8% purity by GC. Distillation of this crude product at 117-120° C., 0.3-1.0 torr gave a 95.7% recovery of product (2) as a colorless oil collected at 112°-119° C.

Example 4

Preparation of 4-[1-(2-Fluoro-4-methanesulfonyl-phenyl)-1H-pyrazolo[3,4-d]pyrimidin-4-yloxy]-piperidine-1-carboxylic acid isopropyl ester (6)

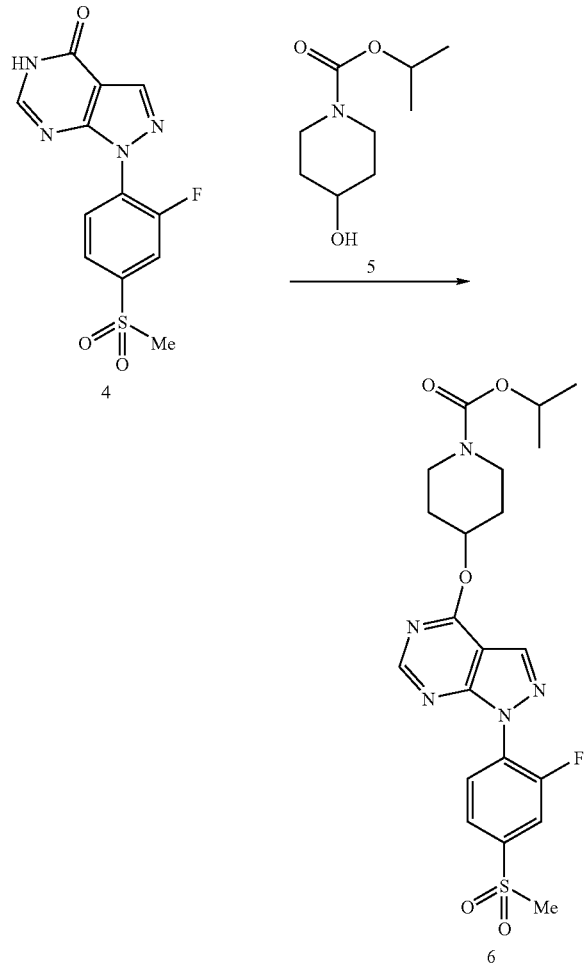

Diisopropyl azodicarboxylate (2.9812 Kg, 1.1713 equivalents) was added to a stirred suspension of (4) (3.8806 Kg, 1.000 equivalent), triphenylphosphine (3.8532 Kg, 1.1671 equivalents), and 4-methylmorpholine (24.7942 Kg) at a rate sufficiently slow to maintain the reaction mixture at 20-30° C. with reactor jacket cooling. The resulting suspension was stirred for 30 minutes at about 25° C. and then heated to 50-55° C. for about two hours. A solution of 4-hydroxypiperidine-1-carboxylic acid isopropyl ester (5) (2.7164 Kg, 1.15255 equivalents) in 4-methylmorpholine (3.0302 Kg) was then added to the reaction mixture at a rate sufficiently slow to maintain the reaction mixture at 45-55° C. About 1.5 hours after the addition of (5) had been completed and then again after another 1.5 hours, more triphenylphosphine (1.4856 Kg, 0.4500 equivalents and then 0.8897 Kg, 0.2695 equivalents) and more diisopropyl azodicarboxylate (1.1445 Kg, 0.4497 equivalents and then 0.6894 Kg, 0.2709 equivalents) were added to the stirred reaction mixture while it continued to be maintained at 50-55° C. After about six more hours of stirring at that temperature, the (6):(4) HPLC peak area ratio was greater than 9:1, and the product was crystallized by cooling the reaction mixture to 0-5° C. and stirring at that temperature for about four hours. The crystallized product was filtered, washed with 4-methylmorpholine (4.3802 Kg, 2° C.) and then with water (10.4754 Kg, ambient temperature), and then recrystallized from 4-methylmorpholine (20.7215 Kg, about 75° C.) by cooling to 2° C. and stirring at that temperature for about two hours. The recrystallized product was filtered, washed with 4-methylmorpholine (4.5893 Kg, 2° C.) and then with water (10.4955 Kg, ambient temperature), and then recrystallized from boiling absolute ethanol (35 Kg) by cooling to 25° C. and stirring at that temperature for about 18 hours. The recrystallized product was collected by filtration, washed with a 2° C. mixture of absolute ethanol (7.657 Kg) and water (3.8276 Kg), and dried to constant weight at 70° C., ≦40 torr to provide product (6) (3.4269 Kg, 57.0% yield).

A similar reaction was conducted using a similar manner as described in this example except for the use of THF as the solvent and portionwise addition of triphenylphosphine, DIAD, and 4-hydroxypiperidine-1-carboxylic acid isopropyl ester (5), which enhanced stirreability and molar efficiency. The multiple crystallization operation from previous iteration of the technology was replaced by a single crystallization in alcohol and aqueous solvent mixture which resulted in higher overall yield and consistent purity for product (6).

Example 5

Preparation of 4-Chloro-1-(2-fluoro-4-methanesulfonyl-phenyl)-1H-pyrazolo[3,4-d]pyrimidine

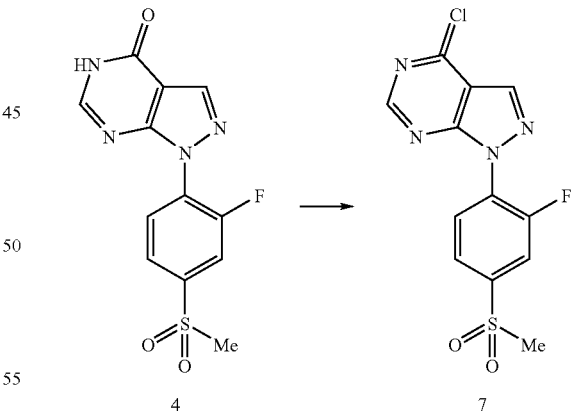

POCl₃ (379.1 g, 2.59 mol) was transferred under nitrogen to a 1 L round bottom flask fitted with a mechanical stirrer, a condenser and a tube connected above the condenser filled with a drying agent (drierite). 1-(2-Fluoro-4-methane-sulfonyl-phenyl)-1,5-dihydro-pyrazolo[3,4-d]pyrimidin-4-one (4) (100 g, 0.324 mol) was added to the reaction vessel, the contents were stirred, and a slurry was obtained. Dimethylformamide (DMF; 9.43 g, 0.129 mol) was added, and the reaction mixture was heated to reflux (oil bath set at 130° C.). After refluxing for 3 h, an additional amount of DMF (9.43 g, 0.129 mol) was added. The resulting mixture was refluxed for another 2 h and then gradually cooled to 55° C. Subsequently, acetone (270 mL) was added. The mixture was further cooled to 23° C. and a precipitate was obtained, which was isolated by filtration. The filtrate was quenched by slow dropwise addition into ice water (1.5 L) with stirring. During the quench, the internal temperature was kept at 0° C. or below by cooling with an ice-salt bath. Product 4-chloro-1-(2-fluoro-4-methanesulfonyl-phenyl)-1H-pyrazolo[3,4-d]pyrimidine (7) crystallized out of the quenched mixtures was isolated by filtration. The solids from both filtrations were combined and washed with water (2×500 mL), 10% aqueous NaHCO$_3$ (2×500 mL), and water (2×500 mL) until the filtrate was neutral. The washed solids were vacuum dried overnight at room temperature and dissolved in methylene chloride (600 mL). The resulting mixture was filtered to remove any residual starting material (4). Hexane (200 mL) was added to the filtrate and methylene chloride was removed by rotary evaporation under reduced pressure. Product crystallized from the hexane solution and was filtered to obtain (7) (95 g; 90%). HPLC analysis, 99.26% (purity, by peak area); $^1$H NMR (Bruker 400 MHz, CDCl$_3$) δ 8.88 (s, 1H, Ar—H), 8.46 (s, 1H, Ar—H), 7.96 (m, 3H, Ar—H), 3.14 (s, 3H, —SO$_2$CH$_3$); mass spec. (electrospray), m/z 327 (M+H).

Example 6

Alternate preparation of 4-[1-(2-Fluoro-4-methane-sulfonyl-phenyl)-1H-pyrazolo[3,4-d]pyrimidin-4-yloxy]-piperidine-1-carboxylic acid isopropyl ester (6)

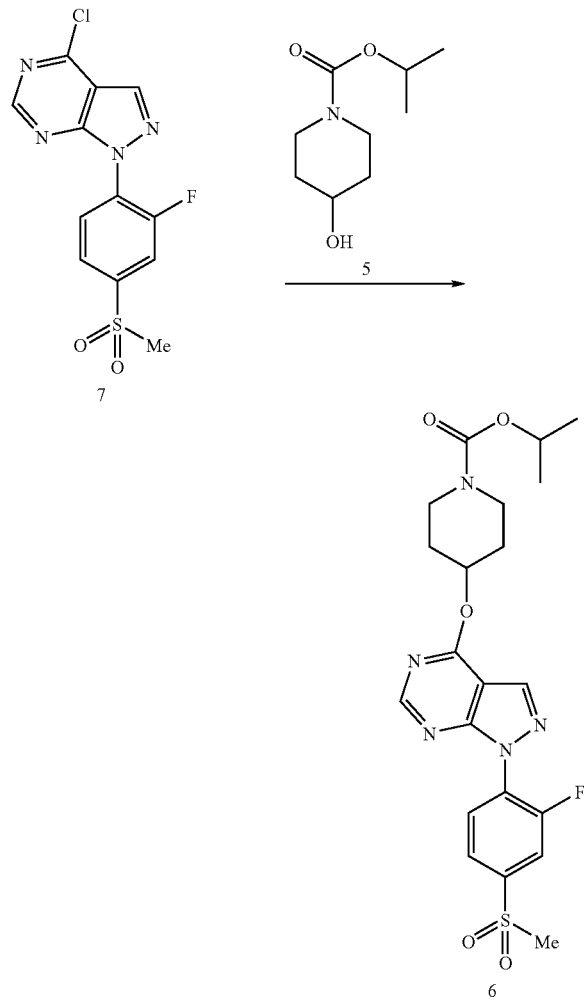

Toluene (1.6 L) was transferred to a 4 L jacketed reaction vessel fitted with a mechanical stirrer, nitrogen inlet and a temperature probe. 4-Chloro-1-(2-fluoro-4-methanesulfonyl-phenyl)-1H-pyrazolo[3,4-d]pyrimidine (7) (97.0 g, 0.297 mol) was added with stirring into the reaction vessel under nitrogen, and a slurry was obtained. The carbamate, 4-hydroxy-piperidine-1-carboxylic acid isopropyl ester (5) (66.57 g, 0.356 mol), was added at room temperature. The reactor was cooled to 12° C. and sodium tert-butoxide (37.09 g, 0.386 mol) was added with stirring. The internal temperature gradually increased to 34° C. due to an exotherm. Then the internal temperature was brought down to 23-25° C. The reaction mixture became a thick slurry and was stirred at room temperature for 2.5 h. The precipitate from the reaction mixture was filtered, washed with toluene (250 mL) followed by water (3×500 mL), and vacuum dried overnight at room temperature. The dried solid product was slurried in EtOH (500 mL) at room temperature, filtered, and washed with water (2.5 L) until the filtrate was neutral. The washed solid product was dissolved in refluxing EtOH (1.3 L), and the resulting clear solution was gradually cooled to room temperature. The product (6) crystallized out and was isolated by filtration and dried overnight in a vacuum oven at 40° C., 20 torr to provide 105.5 g of product (6) (74%). HPLC analysis, >99% (purity, by peak area). $^1$H NMR (Bruker 400 MHz, CDCl$_3$) δ 8.62 (s, 1H, Ar—H), 8.32 (s, 1H, Ar—H), 7.93 (m, 3H, Ar—H), 5.62 (m, 1H, —O—CH—), 4.95 (m, 1H, CH$_3$—C$\underline{H}$—CH$_3$), 3.91 (m, 2H, —CH$_2$—), 3.37 (m, 2H, —CH$_2$—), 3.12 (s, 3H, —SO$_2$CH$_3$), 2.09 (m, 2H, —CH$_2$—), 1.87 (m, 2H, —CH$_2$—), 1.27 (d, 6H, J=8 Hz, C$\underline{H}_3$—CH—C$\underline{H}_3$); mass spec. (electrospray) m/z 478 (M+H).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A process for preparing a compound of Formula I:

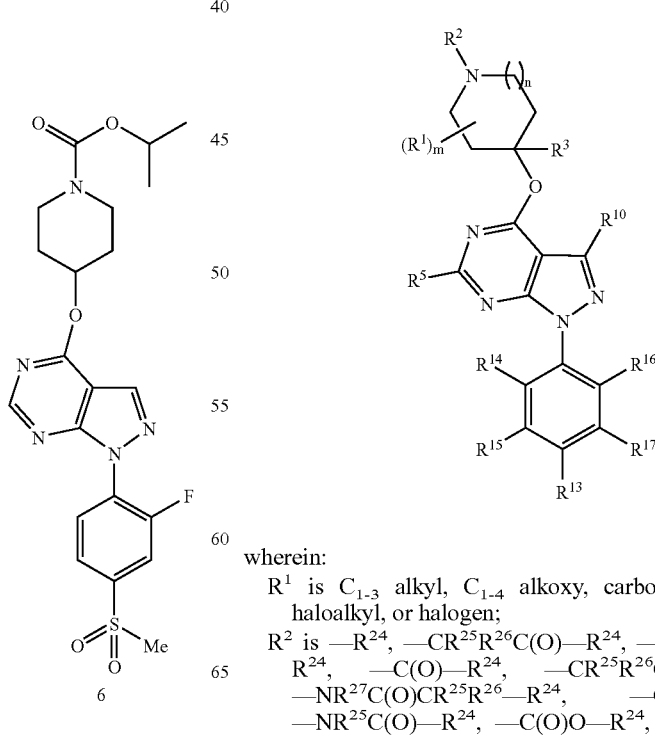

wherein:
R$^1$ is C$_{1-3}$ alkyl, C$_{1-4}$ alkoxy, carboxy, cyano, C$_{1-3}$ haloalkyl, or halogen;
R$^2$ is —R$^{24}$, —CR$^{25}$R$^{26}$C(O)—R$^{24}$, —C(O)CR$^{25}$R$^{26}$—R$^{24}$, —C(O)—R$^{24}$, —CR$^{25}$R$^{26}$C(O)NR$^{27}$—R$^{24}$, —NR$^{27}$C(O)CR$^{25}$R$^{26}$—R$^{24}$, —C(O)NR$^{25}$—R$^{24}$, —NR$^{25}$C(O)—R$^{24}$, —C(O)O—R$^{24}$, —OC(O)—R$^{24}$, —C(S)—R$^{24}$, —C(S)NR$^{25}$—R$^{24}$, —NR$^{25}$C(S)—R$^{24}$, —C(S)O—R$^{24}$, —OC(S)—R$^{24}$, —CR$^{25}$R$^{26}$—R$^{24}$, or —S(O)$_2$—R$^{24}$;

R$^3$ is H, C$_{1-8}$ alkyl or C$_{3-7}$ cycloalkyl, wherein said C$_{1-8}$ alkyl is optionally substituted with C$_{1-4}$ alkoxy, C$_{3-7}$ cycloalkyl, or heteroaryl;

R$^5$ and R$^{10}$ are each, independently, H, C$_{1-5}$ acyloxy, C$_{2-6}$ alkenyl, C$_{1-4}$ alkoxy, C$_{1-8}$ alkyl, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, amino, C$_{1-4}$ alkylamino, C$_{2-8}$ dialkylamino, carboxamide, cyano, C$_{3-6}$ cycloalkyl, C$_{2-6}$ dialkylcarboxamide, C$_{2-6}$ dialkylsulfonamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, hydroxyl, hydroxylamino or nitro; wherein said C$_{2-6}$ alkenyl, C$_{1-8}$ alkyl, C$_{2-6}$ alkynyl and C$_{3-6}$ cycloalkyl are optionally substituted with 1, 2, 3 or 4 substituents selected from C$_{1-5}$ acyl, C$_{1-5}$ acyloxy, C$_{1-4}$ alkoxy, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{2-8}$ dialkylamino, C$_{2-6}$ dialkylcarboxamide, C$_{1-4}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, hydroxyl, hydroxylamino and nitro;

R$^{13}$ is C$_{1-5}$ acyl, C$_{1-6}$ acylsulfonamide, C$_{1-5}$ acyloxy, C$_{2-6}$ alkenyl, C$_{1-4}$ alkoxy, C$_{1-8}$ alkyl, C$_{1-4}$ alkylamino, C$_{1-6}$ alkylcarboxamide, C$_{1-4}$ alkylthiocarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, arylsulfonyl, carbamimidoyl, carbo-C$_{1-6}$-alkoxy, carboxamide, carboxy, cyano, C$_{3-7}$ cycloalkyl, C$_{3-7}$ cycloalkyloxy, C$_{2-6}$ dialkylamino, C$_{2-6}$ dialkylcarboxamide, dialkylthiocarboxamide, guanidinyl, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, C$_{4-7}$ oxo-cycloalkyl, phenoxy, phenyl, sulfonamide, sulfonic acid, or thiol; and wherein said C$_{1-5}$ acyl, C$_{1-6}$ acylsulfonamide, C$_{1-4}$ alkoxy, C$_{1-8}$ alkyl, C$_{1-4}$ alkylamino, C$_{1-6}$ alkylsulfonamide, C$_{1-4}$ alkylsulfonyl, C$_{1-4}$ alkylthio, arylsulfonyl, carbamimidoyl, C$_{2-6}$ dialkylamino, heterocyclic, heterocyclic-carbonyl, heteroaryl, phenoxy and phenyl are optionally substituted with 1 to 5 substituents selected from C$_{1-5}$ acyl, C$_{1-5}$ acyloxy, C$_{2-6}$ alkenyl, C$_{1-4}$ alkoxy, C$_{1-7}$ alkyl, C$_{1-4}$ alkylamino, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, carbo-C$_{1-6}$-alkoxy, carboxamide, carboxy, cyano, C$_{3-7}$ cycloalkyl, C$_{3-7}$ cycloalkyloxy, C$_{2-6}$ dialkylamino, C$_{2-6}$ dialkylcarboxamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heteroaryl, heterocyclic, hydroxyl, nitro, phenyl, and phosphonooxy; and wherein said C$_{1-7}$ alkyl and C$_{1-4}$ alkylcarboxamide are each optionally substituted with 1 to 5 substituents selected from C$_{1-4}$ alkoxy and hydroxy; or R$^{13}$ is a group of Formula (A):

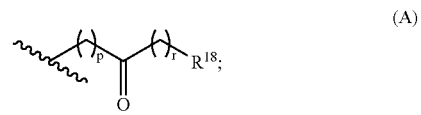

R$^{14}$, R$^{15}$, R$^{16}$, and R$^{17}$ are each, independently, H, C$_{1-5}$ acyl, C$_{1-5}$ acyloxy, C$_{2-6}$ alkenyl, C$_{1-4}$ alkoxy, C$_{1-8}$ alkyl, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, carbo-C$_{1-6}$-alkoxy, carboxamide, carboxy, cyano, C$_{3-7}$ cycloalkyl, C$_{2-6}$ dialkylcarboxamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, hydroxyl or nitro; or two adjacent R$^{14}$, R$^{15}$, R$^{16}$ and R$^{17}$ together with the atoms to which they are attached form a 5-, 6- or 7-membered fused cycloalkyl, cycloalkenyl or heterocyclic group, wherein said 5-, 6- or 7-membered fused group is optionally substituted with halogen;

R$^{18}$ is H, C$_{1-5}$ acyl, C$_{2-6}$ alkenyl, C$_{1-8}$ alkyl, C$_{1-4}$ alkylcarboxamide, C$_{2-6}$ alkynyl, C$_{1-4}$ alkylsulfonamide, carbo-C$_{1-6}$-alkoxy, carboxamide, carboxy, cyano, C$_{3-7}$ cycloalkyl, C$_{2-6}$ dialkylcarboxamide, halogen, heteroaryl or phenyl, and wherein said heteroaryl or phenyl is optionally substituted with 1 to 5 substituents selected independently from C$_{1-4}$ alkoxy, amino, C$_{1-4}$ alkylamino, C$_{2-6}$ alkynyl, C$_{2-8}$ dialkylamino, halogen, C$_{1-4}$ haloalkoxy, C$_{1-4}$ haloalkyl and hydroxyl;

R$^{24}$ is H, C$_{1-8}$ alkyl, C$_{3-7}$ cycloalkyl, phenyl, heteroaryl, or heterocyclic each optionally substituted with 1 to 5 substituents selected from the group consisting of C$_{1-5}$ acyl, C$_{1-5}$ acyloxy, C$_{2-6}$ alkenyl, C$_{1-4}$ alkoxy, C$_{1-7}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-7}$ cycloalkyl, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heteroaryl, heterocyclic, hydroxyl, hydroxylamino, nitro, phenyl, phenoxy, and sulfonic acid, wherein said C$_{1-4}$ alkoxy, C$_{1-7}$ alkyl, C$_{1-4}$ alkylamino, heteroaryl, phenyl and phenoxy are each optionally substituted with 1 to 5 substituents selected from the group consisting of C$_{1-5}$ acyl, C$_{1-5}$ acyloxy, C$_{1-4}$ alkoxy, C$_{1-8}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-7}$ cycloalkyl, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heterocyclic, hydroxyl, hydroxylamino, nitro, and phenyl;

R$^{25}$, R$^{26}$ and R$^{27}$ are each, independently, H or C$_{1-8}$ alkyl;

m is 0, 1, 2, 3, or 4;

n is 0 or 1; and p and r are each, independently, 0, 1, 2 or 3;

said process comprising reacting a compound of Formula II:

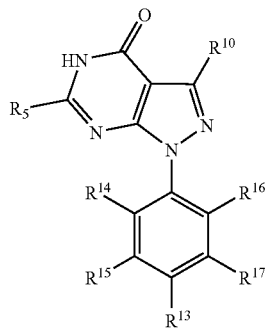

with a compound of Formula III:

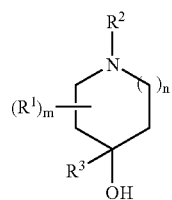

in the presence of a trisubstituted phosphine and a compound having the Formula A':

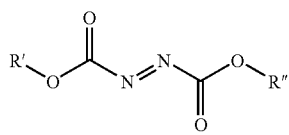

wherein R' and R" are each, independently, $C_{1-10}$ alkyl or $C_{3-7}$ cycloalkyl; to form the compound of Formula I.

2. The process of claim 1 wherein said trisubstituted phosphine is triphenylphosphine.

3. The process of claim 1 wherein R' and R" are both prop-2-yl.

4. The process of claim 1 wherein said phosphine is added in two or more portions.

5. The process of claim 1 wherein said compound of Formula A' is added in two or more portions.

6. The process of claim 1 wherein said reacting is carried out at a temperature of about 35 to about 65° C.

7. The process of claim 1 wherein said reacting is carried out in a solvent.

8. The process of claim 7 wherein said solvent is selected from dimethylformamide, dimethylacetamide, toluene, acetonitrile, propionitril, tetrahydrofuran, N-methylpyrrolidine, and tertiary amine.

9. The process of claim 8 wherein said tertiary amine is 4-methylmorpholine.

10. The process of claim 7 wherein said ether solvent is THF.

11. The process of claim 1 wherein the molar ratio of compound of Formula A' to compound of Formula II is about 2:1 to about 1:1.

12. The process of claim 1 wherein the molar ratio of trisubstituted phosphine to compound of Formula II is about 2:1 to about 1:1.

13. The process of claim 1 wherein the molar ratio of compound of Formula II to compound of Formula III is about 1:1.

14. The process of claim 1 wherein:
$R^2$ is —C(O)O—$R^{24}$;
$R^3$ is H;
$R^5$ is H;
$R^{10}$ is H;
$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol;
$R^{14}$, $R^{15}$, $R^{16}$, and $R^{17}$ are each, independently, H, $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;
n is 1; and
m is 0.

15. The process of claim 1 wherein:
$R^2$ is —C(O)O—$R^{24}$;
$R^3$ is H;
$R^5$ is H;
$R^{10}$ is H;
$R^{13}$ is methylsulfonyl;
$R^{14}$ is F;
$R^{15}$, $R^{16}$, and $R^{17}$ are each H;
$R^{24}$ is prop-2-yl;
n is 1; and
m is 0.

16. The process of claim 1 wherein said compound of Formula II is prepared by the method comprising reacting a compound of Formula IV:

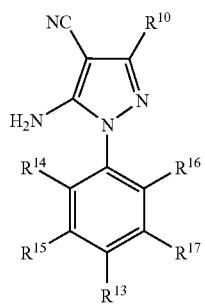

with $R^5CO_2H$ to form said compound of Formula II.

17. The process of claim 16 further comprising sulfuric acid.

18. The process of claim 16 wherein said reacting of said compound of Formula IV is carried out in the presence of aqueous solvent.

19. The process of claim 16 wherein said reacting of said compound of Formula IV is carried out at a temperature of about 80 to about 120° C.

20. The process of claim 16 wherein $R^5CO_2H$ is provided in molar excess relative to said compound of Formula IV.

21. The process of claim 16 wherein $R^5$ is H.

22. The process of claim 16 wherein said compound of Formula IV is prepared by the method comprising reacting a compound of Formula V:

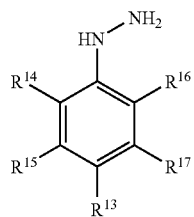

with a compound of Formula VI:

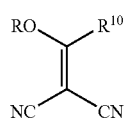

wherein R is $C_{1-4}$ alkyl; to form said compound of Formula IV.

23. The process of claim 22 wherein said reacting of compound of Formula V is carried out in an alcohol.

24. The process of claim 23 wherein said alcohol is methanol.

25. The process of claim 22 wherein said reacting of said compound of Formula V is carried out in the absence of a base.

26. The process of claim 22 wherein the molar ratio of said compound of Formula V to said compound of Formula VI is about 1:1.

27. The process of claim 22 wherein said compound of Formula V and said compound of Formula VI are combined at a temperature of about −20 to about 10° C.

28. The process of claim 22 wherein R is methyl or ethyl.

29. The process of claim 22 wherein $R^{10}$ is H.

30. A process for preparing a compound of Formula II:

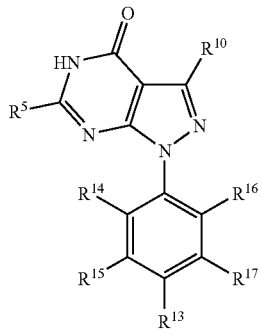

wherein:

$R^5$ and $R^{10}$ are each, independently, H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino or nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy; and wherein said $C_{1-7}$ alkyl and $C_{1-4}$ alkylcarboxamide are each optionally substituted with 1 to 5 substituents selected from $C_{1-4}$ alkoxy and hydroxy; or $R^{13}$ is a group of Formula (A):

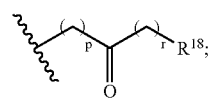

$R^{14}$, $R^{15}$, $R^{16}$, and $R^{17}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl or nitro; or two adjacent $R^{14}$, $R^{15}$, $R^{16}$ and $R^{17}$ together with the atoms to which they are attached form a 5-, 6- or 7-membered fused cycloalkyl, cycloalkenyl or heterocyclic group, wherein said 5-, 6- or 7-membered fused group is optionally substituted with halogen;

$R^{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl is optionally substituted with 1 to 5 substituents selected independently from $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and p and r are each, independently, 0, 1, 2 or 3;
comprising:

a) reacting a compound of Formula V:

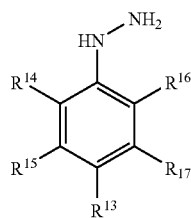

V with a compound of Formula VI:

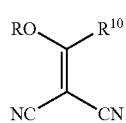

VI wherein R is $C_{1-4}$ alkyl; in the absence of base to form said compound of Formula IV; and b) reacting said compound of Formula IV with $R^5CO_2H$ to form said compound of Formula II.

31. The process of claim 30 wherein said reacting of compound of Formula V is carried out in an alcohol.

32. The process of claim 31 wherein said alcohol is methanol.

33. The process of claim 30 wherein the molar ratio of said compound of Formula V to said compound of Formula VI is about 1:1.1.

34. The process of claim 30 wherein said compound of Formula V and said compound of Formula VI are combined at a temperature of about −20 to about 10° C.

35. The process of claim 30 wherein R is methyl or ethyl.

36. The process of claim 30 wherein $R^{10}$ is H.

37. The process of claim 30 wherein said reacting of said compound of Formula IV is carried out in the presence of aqueous solvent.

38. The process of claim 30 wherein said reacting of said compound of Formula IV is carried out at a temperature of about 80 to about 120° C.

39. The process of claim 30 wherein said $R^5CO_2H$ is provided in molar excess relative to said compound of Formula IV.

40. The process of claim 30 wherein $R^5$ is H.

41. A process for preparing a compound of Formula IV:

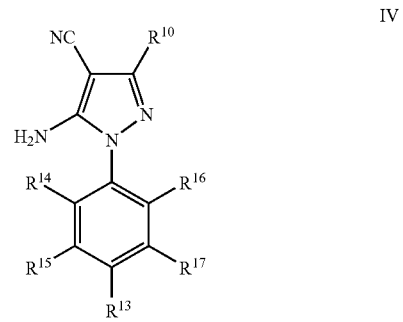

IV wherein:

$R^{10}$ is H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino or nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyloxy, $C_{3-7}$ cycloalkyl, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy; and wherein said $C_{1-7}$ alkyl and $C_{1-4}$ alkylcarboxamide are each optionally substituted with 1 to 5 substituents selected from $C_{1-4}$ alkoxy and hydroxy; or $R^{13}$ is a group of Formula (A):

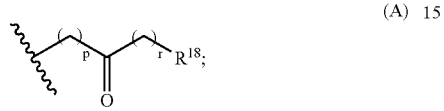

$R^{14}$, $R^{15}$, $R^{16}$, and $R^{17}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl or nitro; or two adjacent $R^{14}$, $R^{15}$, $R^{16}$ and $R^{17}$ together with the atoms to which they are attached form a 5-, 6- or 7-membered fused cycloalkyl, cycloalkenyl or heterocyclic group, wherein said 5-, 6- or 7-membered fused group is optionally substituted with halogen;

$R^{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl is optionally substituted with 1 to 5 substituents selected independently from $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and p and r are each, independently, 0, 1, 2 or 3;

comprising reacting a compound of Formula V:

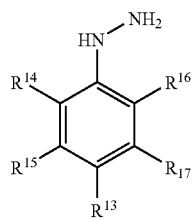

with a compound of Formula VI:

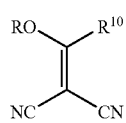

wherein R is $C_{1-4}$ alkyl; in the absence of base, to form said compound of Formula IV.

42. The process of claim 41 wherein said reacting of compound of Formula V is carried out in an alcohol.

43. The process of claim 42 wherein said alcohol is methanol.

44. The process of claim 41 wherein the molar ratio of said compound of Formula V to said compound of Formula VI is about 1:1.1.

45. The process of claim 41 wherein said compound of Formula V and said compound of Formula VI are combined at a temperature of about −20 to about 10° C.

46. The process of claim 41 wherein R is methyl or ethyl.

47. The process of claim 41 wherein $R^{10}$ is H.

48. A process for preparing a compound of Formula I:

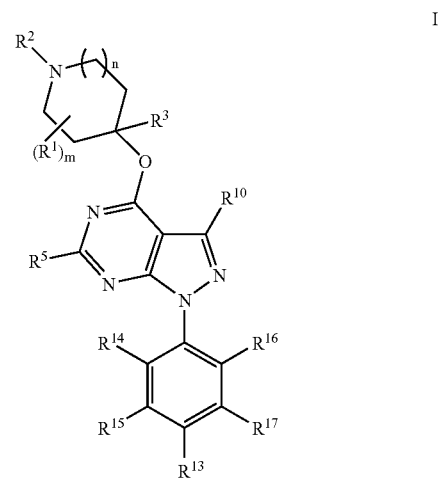

wherein:

$R^1$ is $C_{1-3}$ alkyl, $C_{1-4}$ alkoxy, carboxy, cyano, $C_{1-3}$ haloalkyl, or halogen;

$R^2$ is —$R^{24}$, —$CR^{25}R^{26}C(O)$—$R^{24}$, —$C(O)CR^{25}R^{26}$—$R^{24}$, —$C(O)$—$R^{24}$, —$CR^{25}R^{26}C(O)NR^{27}$—$R^{24}$, —$NR^{27}C(O)CR^{25}R^{26}$—$R^{24}$, —$C(O)NR^{25}$—$R^{24}$, —$NR^{25}C(O)$—$R^{24}$, —$C(O)O$—$R^{24}$, —$OC(O)$—$R^{24}$, —$C(S)$—$R^{24}$, —$C(S)NR^{25}$—$R^{24}$, —$NR^{25}C(S)$—$R^{24}$, —$C(S)O$—$R^{24}$, —$OC(S)$—$R^{24}$, —$CR^{25}R^{26}$—$R^{24}$, or —$S(O)_2$—$R^{24}$;

$R^3$ is H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl;

$R^5$ and $R^{10}$ are each, independently, H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino or nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy; and wherein said $C_{1-7}$ alkyl and $C_{1-4}$ alkylcarboxamide are each optionally substituted with 1 to 5 substituents selected from $C_{1-4}$ alkoxy and hydroxy; or $R^{13}$ is a group of Formula (A):

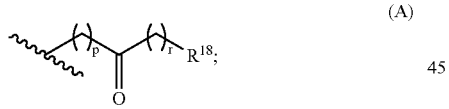

$R^{14}$, $R^{15}$, $R^{16}$, and $R^{17}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl or nitro; or two adjacent $R^{14}$, $R^{15}$, $R^{16}$ and $R^{17}$ together with the atoms to which they are attached form a 5-, 6- or 7-membered fused cycloalkyl, cycloalkenyl or heterocyclic group, wherein said 5-, 6- or 7-membered fused group is optionally substituted with halogen;

$R^{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl is optionally substituted with 1 to 5 substituents selected independently from $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;

$R^{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-4}$ alkoxy, $C_{1-7}$ alkyl, $C_{1-4}$ alkylamino, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, nitro, and phenyl;

$R^{25}$, $R^{26}$ and $R^{27}$ are each, independently, H or $C_{1-8}$ alkyl;

m is 0, 1, 2, 3, or 4;

n is 0 or 1; and p and r are each, independently, 0, 1, 2 or 3;

said process comprising reacting a compound of Formula IIa:

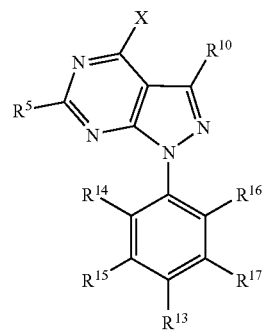

wherein X is halo; with a compound of Formula III:

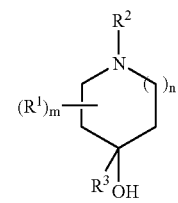

in the presence of an alkoxide salt, to form said compound of Formula I.

49. The process of claim 48 wherein said alkoxide salt is a methoxide, ethoxide, propoxide, isopropoxide, n-butoxide, isobutoxide, or t-butoxide salt.

50. The process of claim 48 wherein said alkoxide salt sodium t-butoxide.

51. The process of claim 48 wherein said reacting is carried out in a solvent.

52. The process of claim 51 wherein said solvent comprises toluene.

53. The process of claim 48 wherein said reacting is carried out at a temperature below about 30° C.

54. The process of claim 48 wherein the molar ratio of said compound of Formula III to said compound of Formula IIa is about 2:1 to about 1:1.

55. The process of claim 48 wherein the molar ratio of alkoxide salt to said compound of Formula IIa is about 2:1 to about 1:1.

56. The process of claim 48 wherein X is Cl.

57. The process of claim 48 wherein:

$R^2$ is —C(O)O—$R^{24}$;

$R^3$ is H;

$R^5$ is H;

$R^{10}$ is H;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol;

$R^{14}$, $R^{15}$, $R^{16}$, and $R^{17}$ are each, independently, H, $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;

n is 1; and m is 0.

58. The process of claim 48 wherein:

$R^2$ is —C(O)O—$R^{24}$;

$R^3$ is H;

$R^5$ is H;

$R^{10}$ is H;

$R^{13}$ is methylsulfonyl;

$R^{14}$ is F;

$R^{15}$, $R^{16}$, and $R^{17}$ are each H;

$R^{24}$ is prop-2-yl;

n is 1; and m is 0.

59. The process of claim 47 wherein said compound of Formula IIa is prepared by a method comprising reacting a compound of Formula II:

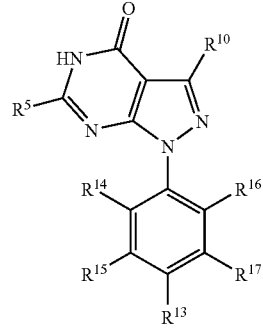

with a halogenating reagent to form said compound of Formula IIa.

60. The process of claim 59 wherein said halogenating reagent is a chlorinating reagent.

61. The process of claim 59 wherein said halogenating reagent is $POCl_3$.

62. The process of claim 59 wherein said reacting of said compound of Formula II with a halogenating reagent is carried out in the presence of a catalyst.

63. The process of claim 62 wherein said catalyst is dimethylformamide.

64. The process of claim 59 wherein said reacting of said compound of Formula II is carried out at a temperature of about 80 to about 140° C.

65. The process of claim 59 wherein the molar ratio of halogenating reagent to the amount of compound of Formula II is about 50:1 to about 2:1.

66. The process of claim 59 wherein the molar ratio of compound of Formula II to amount of catalyst is about 1.3:1 to about 1.2:1.

67. A process for preparing a compound of Formula I:

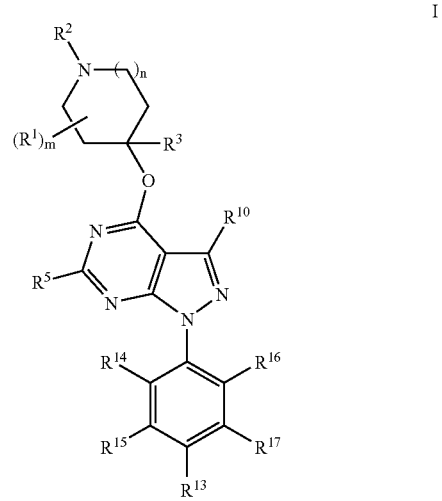

wherein:

$R^1$ is $C_{1-3}$ alkyl, $C_{1-4}$ alkoxy, carboxy, cyano, $C_{1-3}$ haloalkyl, or halogen;

$R^2$ is —$R^{24}$, —$CR^{25}R^{26}C(O)$—$R^{24}$, —$C(O)CR^{25}R^{26}$—$R^{24}$, —$C(O)$—$R^{24}$, —$CR^{25}R^{26}C(O)NR^{27}$—$R^{24}$, —$NR^{27}C(O)CR^{25}R^{26}$—$R^{24}$, —$C(O)NR^{25}$—$R^{24}$, —$NR^{25}C(O)$—$R^{24}$, —$C(O)O$—$R^{24}$, —$OC(O)$—$R^{24}$, —$C(S)$—$R^{24}$, —$C(S)NR^{25}$—$R^{24}$, —$NR^{25}C(S)$—$R^{24}$, —$C(S)O$—$R^{24}$, —$OC(S)$—$R^{24}$, —$CR^{25}R^{26}$—$R^{24}$, or —$S(O)_2$—$R^{24}$;

$R^3$ is H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl;

$R^5$ and $R^{10}$ are each, independently, H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino or nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy; and wherein said $C_{1-7}$ alkyl and $C_{1-4}$ alkylcarboxamide are each optionally substituted with 1 to 5 substituents selected from $C_{1-4}$ alkoxy and hydroxy; or $R^{13}$ is a group of Formula (A):

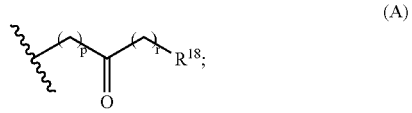

(A)

$R^{14}$, $R^{15}$, $R^{16}$, and $R^{17}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl or nitro; or two adjacent $R^{14}$, $R^{15}$, $R^{16}$ and $R^{17}$ together with the atoms to which they are attached form a 5-, 6- or 7-membered fused cycloalkyl, cycloalkenyl or heterocyclic group, wherein said 5-, 6- or 7-membered fused group is optionally substituted with halogen;

$R^{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl is optionally substituted with 1 to 5 substituents selected independently from $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;

$R^{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-4}$ alkoxy, $C_{1-7}$ alkyl, $C_{1-4}$ alkylamino, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, nitro, and phenyl;

$R^{25}$, $R^{26}$ and $R^{27}$ are each, independently, H or $C_{1-8}$ alkyl;

m is 0, 1, 2, 3, or 4;

n is 0 or 1; and p and r are each, independently, 0, 1, 2 or 3;

said process comprising:

a) reacting a compound of Formula II:

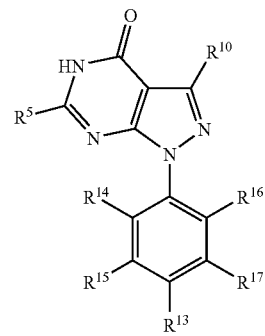

II with a halogenating reagent in the presence of a catalyst to form a compound of Formula IIa.

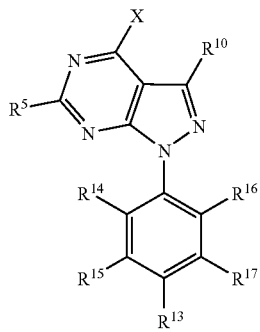

wherein X is halo; and
b) reacting said compound of Formula IIa with a compound of Formula III:

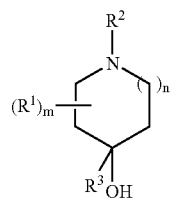

in the presence of an alkoxide salt, to form said compound of Formula I.

68. A process for preparing a compound of Formula IIa:

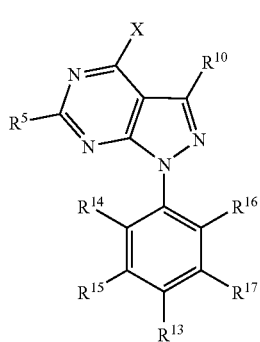

wherein:
X is halo;
$R^5$ and $R^{10}$ are each, independently, H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino or nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R^{13}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy; and wherein said $C_{1-7}$ alkyl and $C_{1-4}$ alkylcarboxamide are each optionally substituted with 1 to 5 substituents selected from $C_{1-4}$ alkoxy and hydroxy; or $R^{13}$ is a group of Formula (A):

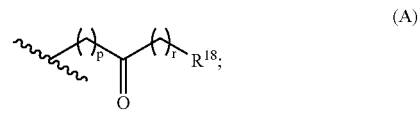

$R^{14}$, $R^{15}$, $R^{16}$, and $R^{17}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl or nitro; or
two adjacent $R^{14}$, $R^{15}$, $R^{16}$ and $R^{17}$ together with the atoms to which they are attached form a 5-, 6- or 7-membered fused cycloalkyl, cycloalkenyl or heterocyclic group, wherein said 5-, 6- or 7-membered fused group is optionally substituted with halogen;
$R^{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl is optionally substituted with 1 to 5 substituents selected independently from $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;

p and r are each, independently, 0, 1, 2 or 3;

said process comprising reacting a compound of Formula II:

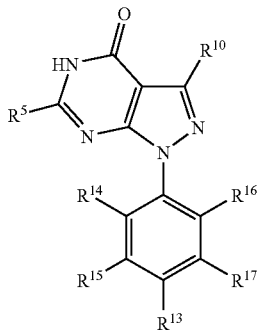

II with a halogenating reagent in the presence of a di-substituted amide catalyst to form said compound of Formula IIa.

69. The process of claim 68 wherein said halogenating reagent is a chlorinating reagent.

70. The process of claim 68 wherein said halogenating reagent is $POCl_3$.

71. The process of claim 68 wherein said catalyst comprises dimethylformamide.

72. The process of claim 68 wherein said reacting of said compound of Formula II is carried out at a temperature of about 80 to about 140° C.

73. The process of claim 68 wherein the molar ratio of halogenating reagent to the amount of compound of Formula II is about 50:1 to about 2:1.

74. The process of claim 68 wherein the molar ratio of compound of Formula II to amount of catalyst is about 1.3:1 to about 1.2:1.

* * * * *